United States Patent [19]

Huang et al.

[11] Patent Number: 5,516,637
[45] Date of Patent: May 14, 1996

[54] METHOD INVOLVING DISPLAY OF PROTEIN BINDING PAIRS ON THE SURFACE OF BACTERIAL PILI AND BACTERIOPHAGE

[75] Inventors: Grace P. Huang; Peter R. Rhode, both of Miami; Jeffrey R. Stinson, Davie; Hing C. Wong, Ft. Lauderdale, all of Fla.

[73] Assignee: Dade International Inc., Deerfield, Ill.

[21] Appl. No.: 258,026

[22] Filed: Jun. 10, 1994

[51] Int. Cl.$^6$ .............................. C12Q 1/68; C12Q 1/70; C12P 21/04; G01N 33/554
[52] U.S. Cl. .................. 435/6; 435/5; 435/7.32; 435/69.7; 435/172.3; 435/320.1; 536/23.4
[58] Field of Search .................. 435/6, 69.7, 5, 435/7.32, 172.3, 320.1; 536/23.4

[56] References Cited

U.S. PATENT DOCUMENTS

| | | | |
|---|---|---|---|
| 5,223,409 | 6/1993 | Ladner et al. | 435/69.7 |
| 5,348,867 | 9/1994 | Georgiou et al. | 435/69.7 |

FOREIGN PATENT DOCUMENTS

| | | |
|---|---|---|
| 0264150 | 9/1987 | European Pat. Off. . |
| 2699538 | 12/1992 | France . |
| 91/18980 | 5/1991 | WIPO . |
| 91/19818 | 6/1991 | WIPO . |
| WO92/01047 | 1/1992 | WIPO . |
| WO92/20791 | 11/1992 | WIPO . |
| 93/18163 | 3/1993 | WIPO . |
| WO93/10214 | 5/1993 | WIPO . |

OTHER PUBLICATIONS

Dueñas et al (1994) "Intra- and Extracellular expression of an scFv antibody fragment in *E. coli*: Effect of bacterial strains and" etc. BioTechniques 16(3)476–483.

Harrison et al (1990) "Presentation of foreign antigenic determinants at the bacterial cell surface using the TraT lipoprotein" Res. Microbiol. 141:1009–1012.

Söderlind et al (1992) "Phage display technology in antibody engineering: Design of phagemid vectors and in vitro maturation systems." Immun. Rev. 130:109–124.

Little et al. (1994) "Surface display of antibodies" Biotech. Adv. 12:539–555.

L. S. Frost and W. Paranchych, MGG 1988, 213:134–139.

K. A. Ippen–Ihler and E. G. Minkley, Jr., Ann. Rev. Genet. 1986, 20:593–624.

G. Georgiou, et al., TIBTECH, Jan. 1993 (vol. 11) 6–10.

W. D. Paiva, et al., J of Biol. Chem., vol. 267, No. 36, pp. 26191–26197 (1992).

T. Grossman, et al., J. of Bacteriology, Mar. 1990, pp. 1174–1179, vol. 172 No. 3.

M. Hoefnung, Methods in Cell Biology, vol. 34, pp. 77–105 (1991).

J. K. Scott, Techniques, 1992 pp. 241–245.

P. Fuchs, et al; Biotechnology vol. 9 Dec. 1991 pp. 1370–1372.

Grussenmeyer et al. (1985) "Complexes of polyoma virus medium T antigen and cellular proteins" Proc. Natl. Acad. Sci. USA 82:7952–7954.

Newton et al., *Immune Response to Cholera Toxin Epitope Inserted in Salmonella Flagellin*, Science, vol. 244:70–72.

Frost, et al., *A Sequence of The F traALE Region that Includes the Gene for F Pilin*, Journal of Bacteriology, vol. 160:395–402, Oct. 1994.

(List continued on next page.)

Primary Examiner—Mindy Fleisher
Assistant Examiner—Scott D. Priebe
Attorney, Agent, or Firm—David S. Resnick

[57] ABSTRACT

The present invention relates to a fusion protein, comprising a pilin protein or a portion thereof and a heterologous polypeptide (target protein). In a preferred embodiment it relates to a method for displaying the target protein on the outer surface of a bacterial host cell capable of forming pilus. In certain embodiments, it is desirable that the pilus is a receptor for bacteriophage attachment and infection. The F pilus is preferred.

14 Claims, 20 Drawing Sheets

OTHER PUBLICATIONS

Frost, et al., *Characterization and Sequence Analysis of Pilin from F-Like Plasmids*, Journal of Bacteriology, vol. 164:1238–1247.

McCafferty, et al., *Phage antibodies: filamentous phage displaying antibody variable domains*, Letters to Nature, vol. 348:552–554.

Thiry et al. (1989) "Cloning of DNA sequences encoding foreign peptides and their expression in the K88 pili." Applied and Environmental Microbiology 55(4):984–993.

Yamagishi et al. (1990) "Mutational analysis of structure-activity relationships in human tumor necrosis factor alpha." Protein Engineering 3(8):713–719.

Dueñas et al. (1994) "Clonal selection and amplification of phage displayed antibodies by linking antigen recognition and phage replication" Bio/Technology 12:999–1002.

Barbas et al (1991) Assembly of combinatorial antibody libraries on phage surfaces: The gene III site. Proc. Natl. Acad. Sci. USA 88:7978–7982.

PCR PRIMERS
traA LEADER FORWARD - OPR5
5'-GGGGGGAATTCTATCCGAAATTGAGGTAACTTATG-3' (SEQ ID NO:1)
traA BACK - OPR6
5'-GGGGGGTCTAGATTATCAGAGGCCAACGACGGCCATAAC-3' (SEQ ID NO:2)
traA LEADER BACK - OPR7
5'-GGGGGGATCCCCATGGCCAGCTGCGGGAAGAACATCATCAG-3' (SEQ ID NO:3)
traA GENE FORWARD - OPR8
5'-GGGGGGATCCGGCGCCGGCAGCAGTGGTCAGGACCTGATG-3' (SEQ ID NO:4)

TA1 HC FORWARD - JS135
5'-CACTTGGCCATGGCCGAGGTTCAGCTGCAGCAG-3' (SEQ ID NO:5)
TA1 HC BACK - JS134
5'-GCTGCCACCGCCACCTGAGGAGACGGTGACTGAG-3' (SEQ ID NO:6)
TA1 LC FORWARD - JS133
5'-GGAGGCGGCGGTTCTGATATTGTGATGACTCAGGC-3' (SEQ ID NO:7)
TA1 LC BACK - JS153
5'-TTCATAGGCGGCCGCACTAGTAGCMCGTTTCAGYTCCARC-3' (SEQ ID NO:8)

α-CKMB HC FORWARD - JS155
5'-GCCGGCCATGGCCCAGGTBCARCTKMARSARTC-3' (SEQ ID NO:9)
α-CKMB HC BACK - JS160
5'-GCTGCCACCGCCACCTGMRGAGACDGTGASTGARG-3' (SEQ ID NO:10)
α-CKMB LC FORWARD - JS148
5'-GGAGGCGGCGGTTCTGACATTGTGMTGWCACAGTC-3' (SEQ ID NO:11)
α-CKMB LC BACK - JS154
5'-TTCATAGGCGGCCGCACTAGTAGCMCGTTTKATYTCCARC-3' (SEQ ID NO:12)

(GGGS)₃ LINKER PRIMERS - JS137
5'-GGTGGCGGTGGCAGCGGCGGTGGTGGTTCCGGAGGCGGCGGTTCT-3' (SEQ ID NO:13)
JS139
5'-AGAACCGCCGCCTCCGGAAGGAGGACCGCCGCTGCCACCGCCACC-3' (SEQ ID NO:14)

EE TAG OLIGONUCLEOTIDES
OPR15
5'-CATGGCGGCCGGCAGCGCGGCCGCTGAGGAAGAAGAGTACATGCCGATGGAAG-3' (SEQ II NO:15)
OPR16
5'-GCGCCTTCCATCGGCATGTACTCTTCTTCCTCAGCGGCCGCGCTGCCGGCCGC-3' (SEQ II NO:16)

FIG. 3

```
                                  >EcoRl
                                    |
GAAAC AGCTA TGAC C ATGAT TACGA ATTCT ATCCG A AATT GAGG T AACTT ATG AAT GCT
CTTTG TCGAT ACTG G TACTA ATGCT TAAGA TAGGC T TTAA CTCC A TTGAA TAC TTA CGA
                                                              M   N   A>

P_lac        -10 REGION                      traA RBS

GTT TTA AGT GTT CAG GGT GCT TCT GCG CCC GTC AAA AAG AAG TCG TTT TTT TCC
CAA AAT TCA CAA GTC CCA CGA AGA CGC GGG CAG TTT TTC TTC AGC AAA AAA AGG
 V   L   S   V   Q   G   A   S   A   P   V   K   K   K   S   F   F   S> traA LEADER

AAA TTC ACT CGT CTG AAT ATG CTT CGC CTG GCT CGC GCA GTG ATC CCG GCT GCT
TTT AAG TGA GCA GAC TTA TAC GAA GCG GAC CGA GCG CGT CAC TAG GGC CGA CGA
 K   F   T   R   L   N   M   L   R   L   A   R   A   V   I   P   A   A>

>NcoI   >SfiI           >NotI
                                |       |               |
GTT CTG ATG ATG TTC TTC CCG CAG CTG GCC ATG GCG GCC GGC AGC GCG GCC GCT
CAA GAC TAC TAC AAG AAG GGC GTC GAC CGG TAC CGC CGG CCG TCG CGC CGG CGA
 V   L   M   M   F   F   P   Q   L   A   M   A   A   G   S   A   A   A>

CLONING SITES
                              >KasI
                                |
GAG GAA GAA GAG TAC ATG CCG ATG GAA GGC GCC GGC AGC AGT GGT CAG GAC CTG
CTC CTT CTT CTC ATG TAC GGC TAC CTT CCG CGG CCG TCG TCA CCA GTC CTG GAC
 E   E   E   E   Y   M   P   M   E   G   A   G   S   S   G   Q   D   L>

EE TAG
```

FIG. 4A

```
 *              *              *              *              *
ATG GCA AGC GGT AAC ACC ACG GTT AAG GCG ACC TTC GGT AAG GAC TCC AGT GTT
TAC CGT TCG CCA TTG TGG TGC CAA TTC CGC TGG AAG CCA TTC CTG AGG TCA CAA
 M   A   S   G   N   T   T   V   K   A   T   F   G   K   D   S   S   V>
                                  traA GENE

*              *              *              *              *              *
GTT AAA TGG GTT GTT CTG GCT GAA GTT CTG GTC GGT GCT GTC ATG TAC ATG ATG
CAA TTT ACC CAA CAA GAC CGA CTT CAA GAC CAG CCA CGA CAG TAC ATG TAC TAC
 V   K   W   V   V   L   A   E   V   L   V   G   A   V   M   Y   M   M>
                              traA GENE (CONT.)

*              *              *              *              *              *
ACC AAA AAC GTC AAG TTC CTG GCC GGT TTT GCC ATC ATC TCT GTA TTT ATT GCT
TGG TTT TTG CAG TTC AAG GAC CGG CCA AAA CGG TAG TAG AGA CAT AAA TAA CGA
 T   K   N   V   K   F   L   A   G   F   A   I   I   S   V   F   I   A>

>XbaI
                                            |
 *              *              *            | *            *              *
GTG GTT ATG GCC GTC GTT GGC CTC TGA TAA TCT AGAGT CGACC TGCAG GCATG
CAC CAA TAC CGG CAG CAA CCG GAG ACT ATT AGA TCTCA GCTGG ACGTC CGTAC
 V   V   M   A   V   V   G   L   *   *>    (SEQ ID NO:18)
                              STOP CODONS
>Hind3
 |
 |     *              *              *              *              *
CAAGC TTGGC ACTGG CCGTC GTTTT ACAAC GTCGT GACTG GGAAA ACCCT
GTTCG AACCG TGACC GGCAG CAAAA TGTTG CAGCA CTGAC CCTTT TGGGA    (SEQ ID NO:17)
```

FIG. 4B

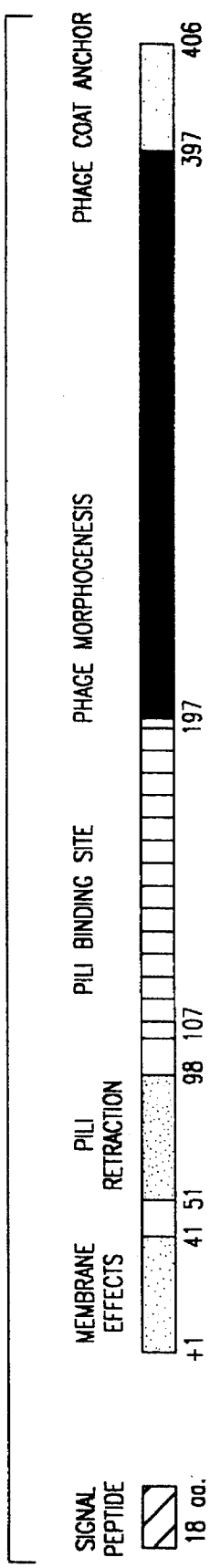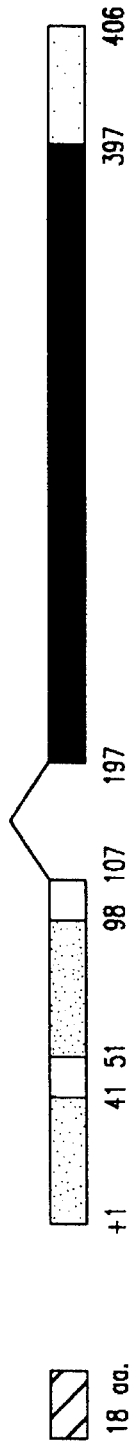
FIG. 10

NORMAL INFECTION
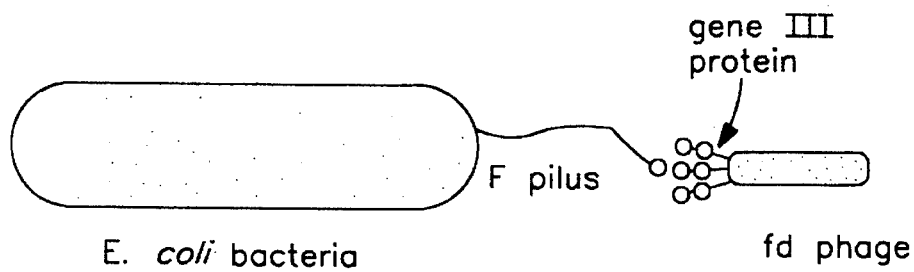
1) BINDING OF PHAGE TO THE TIP OF THE PILUS
2) DEPOLYMERIZATION OF PILUS
3) ENTRY OF THE PHAGE INTO THE CELL
ANTIGEN/ANTIBODY DRIVEN INFECTION
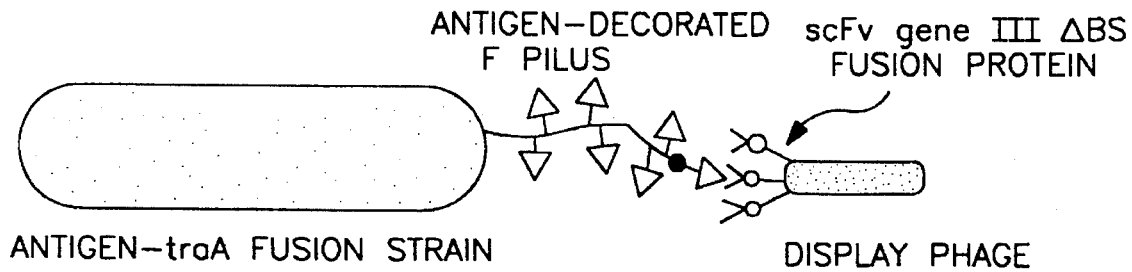
NORMAL GENE III PROTEIN/PILIN INTERACTION IS
REPLACE BY ANTIGEN/ANTIBODY INTERACTION
FIG. 11

METHOD INVOLVING DISPLAY OF PROTEIN BINDING PAIRS ON THE SURFACE OF BACTERIAL PILI AND BACTERIOPHAGE

The present invention relates generally to the exportation and display of polypeptides and proteins on the surface of bacteria. Methods are disclosed providing for display, modification, selection and purification of proteins, including antigenically active proteins, specific binding proteins and enzymatically active proteins.

BACKGROUND OF THE INVENTION

The expression of polypeptides on the surface of bacteria and bacteriophage has been pursued for several years, in part because of interest in recombinant antibody production. Many other potential applications exist, including the production of genetically-engineered whole cell adsorbents, construction of "peptide libraries", cell bound enzymes, and use as live vaccines or immunogens to generate antibodies. [See, WO92/01047 and WO93/10214.]

In bacteria, one approach to obtaining surface expressed foreign proteins has been the use of native membrane proteins as a carrier for a foreign protein. In general, most attempts to develop methods of anchoring proteins on a bacterial surface have focused on fusion of the desired recombinant polypeptide to a native protein that is normally exposed on the cell's exterior with the hope that the resulting hybrid will also be localized on the surface. However, in most cases, the foreign protein interferes with localization, and thus, the fusion protein is unable to reach the cell surface. These fusions either end up at incorrect cellular locations or become anchored in the membrane with a secreted protein domain facing the periplasm [Murphy, et al., *J. Bacteriol.*, 172:2736 (1990)].

Francisco, et al., [*Proc. Natl. Acad. Sci.*, 89:2713 (1992)] reported constructing a surface-expression vehicle consisting of the Ipp N-terminal targeting sequence fused to a sequence derived from ompA leaving the C-terminus exposed on the external side of the outer membrane. These fusions have been reported to export a number of heterologous proteins to the *E. coli* surface, including β-lactamase, single-chain Fv antibody and a cellulose binding protein [WO93/10214]. In addition, Fuschs, et al., [Bio/Technology, 9:1369 (1991)] reported that a fusion between the *E. coli* peptidoglycan-associated lipoprotein (pal) and a lysozyme-binding single-chain Fv antibody fragment could be detected on the surface of bacteria. However, in these systems, the displayed proteins were affixed to the cell surface, and thus in order to isolate purified protein, the DNA encoding the protein must be subcloned to another system.

Systems have been developed for displaying recombinant proteins, including antigens and antibodies, on the surface of filamentous bacteriophage [see, for example, WO92/01047]. In these systems, the recombinant protein is fused to the phage coat proteins expressed by either gene III (minor coat protein) or gene VIII (major coat protein). The display phage can be selectively enriched based on the binding properties of the recombinant protein. In addition, the phage carries a vector for expression of the recombinant protein-gene III fusion allowing propagation of the display phage. One of the advantages of this system is that a large library of different proteins such as Fab or single-chain Fv antibody fragments can be displayed on the phage and selected for on the basis of their binding characteristics. One disadvantage is that the number of heterologous protein molecules displayed by the phage is low, thus complicating the selection process. Another disadvantage with phage systems, as well as current bacterial systems is that the enrichment or panning process requires a significant amount of purified binding protein, e.g., antigen, and involves repeated rounds of selection and re-amplification that may result in the isolation of recombinant proteins, e.g., single-chain antibodies, with low binding affinities.

A display system combining the benefits of bacterial display and phage display has yet to be developed. Such a system would be very desirable.

It would also be desirable to have a method that can be used for cloning and protein purification with out the need for subcloning.

It would be desirable to have a display and selection method that eliminates the need for panning and purification of binding protein.

SUMMARY OF THE INVENTION

The present invention relates to a fusion protein, comprising a pilin protein or a portion thereof and a heterologous polypeptide (target protein). In a preferred embodiment it relates to a method for displaying the target protein on the outer surface of a bacterial host cell capable of forming pilus. In certain embodiments, it is desirable that the pilus is a receptor for bacteriophage attachment and infection. The F pilus is preferred.

The fusion protein is expressed from a chimeric DNA having a DNA segment encoding a leader amino acid sequence capable of mediating secretion of the fusion protein, a DNA segment encoding pilin subunits, e.g., the traA gene product, and a DNA segment encoding the target protein. The DNA segments are positioned such that expression of the fusion protein results in display of the target protein on the surface of the pilus. The pilus is preferably anchored to the cell surface of a bacteria forming what is referred to as a "display bacteria."

The chimeric DNA may be integrated into the bacterial cell chromosome or be carried by a vector. In certain preferred embodiments, expression of the fusion protein may be regulated by an inducible promoter, e.g., lac. Bacteria displaying a particular protein may be selected, for example, using antibody affinity. The fusion protein can be detached from selected cells. If desired, the target protein may be separated from the pilin protein and further purified.

The present invention further relates to a method for selecting and isolating specific binding pairs, e.g., antigen-antibody, receptor-ligand. In accordance with this method, a display bacteria is formed in which one protein of the specific binding pair is displayed and replaces the natural receptor for bacteriophage infection. The phage is also altered such that the normal pilin interaction domain is substituted with the other member of the specific binding pair or a library of proteins containing potential binding members. Alternatively, the bacteria display a library of protein containing potential binding proteins. The display phage is then contacted with the display bacteria. Phage displaying one member of the specific binding pair recognize and infect the display bacteria displaying the other member based on the protein-protein interactions between the displayed proteins. The phage genome is then internalized by the display bacteria. These bacteria can then be selected by, for example, identifying of a marker gene, i.e., antibiotic resistance, transferred from the phage to the display bacteria. In addition, phage displaying high affinity binding proteins infect and replicate at a higher rate than the phage displaying lower affinity binding proteins. This allows phage displaying a library of potential binding proteins to be screened for high affinity binding since these phage will be selectively enriched with continued growth in cultures of the display bacteria. DNA encoding members of the specific binding pair can then isolated from the display bacterial host.

As used herein, bacteriophage also include phage rescued from an *E. coli* host carrying a phagemid vector encoding the fusion protein. While such phage are capable of infecting the display bacteria, since they lack the necessary phage genes they cannot produce particles for reinfection and thus cannot be used in method where reinfection is desired.

In one embodiment, the DNA encoding a member of a specific binding pair is mutagenized, e.g., by use of a mutator strain, and the method of the present invention used to select a member of a specific binding pair having an altered binding affinity, e.g., increased affinity. In another embodiment, compounds can be tested for their ability to affect, e.g., inhibit or potentiate, the specific binding pair interaction.

```
OPR1-    5'-GGG GGG AGC TCT CTG CAA AGG AGA CAG TCA TAA TGA AAT ACC TAT TGC   (SEQ ID NO: 19)
         CTA CGG CAG CCG CTG GAT TG-3'

OPR2-    5'-GGG GGG CCG CGG CCG CGG CCA TGG CCG GCT GGG CCG CGA GTA ATA ACA   (SEQ ID NO: 20)
         ATC CAG CGG CTG CCG TAG-3'

OPR3-    5'-GGG GGG CCG CGG CCG CGG AGG AAG AAG AGT ACA ACC CGA ACG AAG GCG   (SEQ ID NO: 21)
         CCG CCT AGA CTG TTG AAA GTT GTT TAG CAA AAC CTC-3'

OPR4-    5'-GGG CCG AAT TCC TAT TAA GAC TCC TTA TTA CGC AGT ATG TTA GC-3'    (SEQ ID NO: 22)

OGH1-    5'-GGG GGG ACT AGT GCG GCC GCG GGC GCC GCT GAA ACT GTT GAA AGT TGT    (SEQ ID NO: 23)
         TTA GC-3'

OGH107-  5'GGG GGG GGA TCC AGA GGG TTG ATA TAA GTA TAG CC-3'    (SEQ ID NO: 24)
```

Target proteins useful in the present invention include peptides, proteins, e.g., hormones, enzymes, inhibitors, and receptors, antigens, antibodies including antibody fragments, single-chain antibodies and a member of a specific binding pair. Alternatively, the target protein may be a derivative or analog of any such proteins. Specific binding pairs include any pair of molecules, either naturally derived or synthetically produced in which one of the pair has an area which binds to the other molecule. Examples of such specific binding pairs include, for example, antigen-antibody, hormone-hormone receptor, receptor-ligand, enzyme-substrate and IgG-protein A.

Other uses for the protein display methods of the present invention include, for example, epitope mapping, screening of antibody libraries and live bacterial vaccines.

BRIEF DESCRIPTION OF THE DRAWINGS

FIG. 3 sets forth oligonucleotides (SEQ ID NOS: 1–16) used in PCR amplification and vector construction. Relevant restriction sites are underlined.

FIGS. 4A and 4B set forth the nucleotide (SEQ ID NO: 17) and amino acid sequence (SEQ ID NO: 18) of the pPR35 traA fusion region.

FIG. 10 shows the fd gene III protein structure function analysis.

FIG. 11 illustrates the bacteriophage/pilin interaction system.

DETAILED DESCRIPTION OF THE INVENTION

Figure 1:
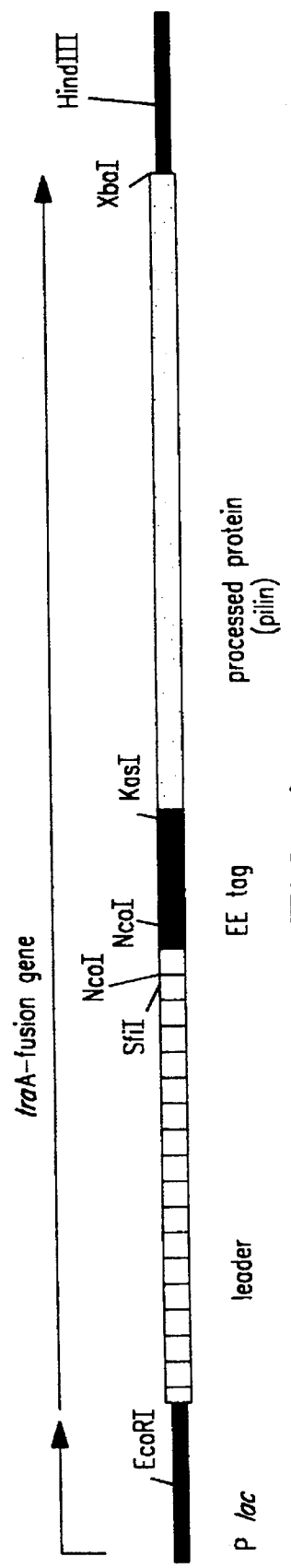
FIG. 1 is a diagram showing the features of the traA expression vector pPR35.

F pili are filaments found on the surface of cells carrying the F plasmid. They are essential for establishing competent mating pairs during bacterial conjugation [see, Ippen-Ihler and Minkley, *Ann. Rev. Genet.*, 20:593–624 (1986)] and are the site of attachment for three classes of bacteriophage, R17, QB, and fd [Paranchych, *Cold Spring Harbor Laboratory*, pp. 85–111 (1975)]. The top of the pilus is thought to be involved in the recognition of a recipient cell (mating pair formation) or another donor cell (surface exclusion) and is the site of attachment of the filamentous phage, fd. The sides of the pilus are the site of attachment of two types of spherical phages, exemplified by R17 and QB.

Synthesis of the F pilus requires 13 or more gene products encoded by the transfer region on the F plasmid [Ippen-Ihler and Minkley, *supra* (1986)]. The F pilus is composed of a single subunit of 7,200 daltons encoded by the traA gene. The initial traA gene product is propilin (13,200 daltons) which contains 51-amino acid leader sequence. The pilin subunit is acetylated at the amino-terminus and traG is thought to be involved in this process [Ippen-Ihler and Minkley *supra* (1986); Willetts and Skurray, *American Society for Microbiology*, 2:1110–1133 (1987)].

F-like plasmids encode four known types of pili which can be distinguished serologically [Lawn and Meynell *J. Hyg.*, 68:683–694 (1978); Meynell *International Conference on Pili*, pp. 207–234 (1978)], by phage sensitivity patterns or surface exclusion [Willetts and Maule, *Genet. Res.* 47:1–11 (1986)]. These pili are also thought to recognize different receptors on the surface of the recipient cell [Havekes, et al., *Mol. Gen. Genet.*, 155:185–189 (1977)]. Representative pilin genes from four types have been sequenced [(Frost, et al., *J. Bacteriol.*, 164:1238–1247 (1985)] and the changes in protein sequence are found in the amino-terminus [Finlay, et al., *J. Bacteriol.*, 163:331–335 (1985)], with the carboxy-terminus influencing the antigenicity of the protein [Frost, et al., *supra* (1985)]. The four pilus types vary in their ability to attach to F-specific phages [Meynell, *supra* (1978)], which reflects changes in pilin sequence. However, the amino-terminus does not seem to be involved in phage attachment since pili with different amino-terminal attach fd phage equally [Frost, et al., *supra* (1985); Finlay, et al. *J. Bacteriol.*, 168:990–998 (1986)]. The changes in sequence which probably affect phage binding occur at residues 11 and 14 in type IV pilin (represented by the R100-1 plasmid) and at the carboxy-terminus in Type III pilin (represented by the R1-19 plasmid). Studies with polyclonal antisera [Worobec, et al., *J. Bacteriol.*, 167:660–665 (1986)] and monoclonal antisera [Frost, et al., *J. Bacteriol.*, 168:192–198 (1986)] have shown that the major epitope at the amino-terminus is exposed in a tip-specific manner at the end of the pilus. The minor epitope(s) which involve the carboxy-terminus of the pilin protein are exposed on the sides of the pilus.

The method of the present invention relates to displaying a heterologous polypeptide (target protein) on the outer surface of a bacterial host cell. This method comprises expression of a fusion protein, comprising a pilin protein or a portion thereof and the target protein in a bacterial host cell capable of forming a pilus. The fusion protein being expressed from a chimeric DNA having a DNA segment encoding a leader amino acid sequence capable of mediating secretion of the fusion protein, a DNA segment encoding the pilin protein and a DNA segment encoding the target protein, said DNA segments being operably linked such that the host cell displays the target protein on its surface.

Any bacterial strain capable of forming a pili can be used as a bacterial host cell for the expression of the chimeric DNA. Strain capable of forming an F or F-like pili are preferred. Such strains include *E. coli* (Ippen-Ihler, et al.), *Salmonella typhimurium* [Artz, S. Holzschu, D., Blum, P., and Shand, R. (1983) Gene 26, 147–158], as well as other gram-negative bacterial carrying F-like plasmids. *E. coli* is the preferred host cell. Particularly preferred *E. coli* strains include XL1B [Bullock, W. O. et al. (1987) *Bio/Techniques* 5, 376–378] and DH5αF'[Woodcock, D. M. et al. (1989) *Nucleic Acids Res.* 17,3469–3478]. In certain embodiments, *E. coli* strains that overexpress pili are preferred. Such strains include, for example, those that carry the depressed F-like plasmid pED208 [Frost, L. S., et al., (1985) J. Bacteriol. 164, 1238–1247].

The first component of the chimeric DNA is a DNA segment encoding a leader amino acid sequence capable of mediating secretion of the fusion protein, i.e., directing the fusion protein to the external membrane surface. Such sequences include, for example, the traA leader sequence, the phoA leader or the pelB leader. The traA leader sequence is preferred. The traA leader sequence may be obtained by PCR amplification from an F plasmid template. F plasmids are available, for example, from bacterial cells such as *E. coli* XL1B. A representative traA leader sequence is set forth in FIG. 4.

The second component of the chimeric DNA is a DNA segment encoding the pilin protein subunit or a portion thereof capable of displaying the target protein on the cell surface. Mutation analysis suggest that the region of the pilin subunit between amino acids 18 to 68 contain elements required for pilus assembly (Frost et al., Mol. Gen. Genet. 213:134–139 (1988)). The traA gene product is preferred.

Hydropathy profiles the F-pilin suggests that the molecule is organized into four domains [Paiva, W. D., et al., (1992) J. Biol. Chem. 267, 26191–26197]. Variability in the number and type of amino acids present in the N-terminal domain is observed for different F-like pilin proteins [Frost, L. S. et al (1985)], suggesting that this region may be dispensable for pili assembly and display of on the cell surface. As described above, the traA gene encodes the 51 amino acid pilin leader and the 70 amino acid mature pilin protein. TraA genes have been cloned and sequenced from F and a number of related F-like plasmids, including ColB2 (Group II), R1-19 (Group III), R100-1 (Group IV), and pED208 (Group V)[Finlay, B. B. et al, (1984) J. Bactriol. 160:402–407; Frost, L. S. et al (1984) J. Bacteriol. 160:395–401; Frost, L. S. et al (1985); Finlay, B. B. et al (1986) J. Bacteriol. 168:990–998]. These genes show a high homology with each other and encode pilin proteins that comprise morphologically and functionally similar structures, as emphasized by the formation of mixed pili by cells carrying different F-like plasmids [Lawn, A. M., et al (1971) Ann. Institute Pasteur 120:3-8]. Since the sequences of various traA genes are available, the DNA encoding the traA gene product can be readily isolated from a number of sources, including for example, PCR amplification from an F plasmid template. See, Example 1 for the details of the PCR amplification. A representative F plasmid traA gene sequence is set forth in FIG. 4.

Target proteins, encoded by the third component of the chimeric DNA, can include peptides, proteins, e.g., hormones, enzymes, inhibitors, and receptors, antigens, antibodies including antibody fragments (e.g., Fab, Fab' and F(ab')$_2$) single-chain antibodies and a member of a specific binding pair. Alternatively, the target protein may be a derivative or analog of any such proteins. Specific binding pairs include any pair of molecules, either naturally derived or synthetically produced, in which one of the pair has an area which binds to the other molecule. Examples of such specific binding pairs include, for example, antigen-antibody, hormone-hormone receptor, receptor-ligand, enzyme-substrate and IgG-protein A.

The nucleotide sequence of many target proteins are readily available through a number of computer data bases, for example, GenBank, EMBL and Swiss-Prot. Using this information, a DNA segment encoding the desired target protein may be chemically synthesized or, alternatively, the such a DNA segment may be obtained using routine procedures in the art, e.g, PCR amplification.

The DNA segments are positioned such that expression of the fusion protein results in the display of the target protein on the cell surface, forming what is referred to as a "display bacteria."

The target protein may be fused to any portion of the pilin protein that is capable of displaying the target protein on the cell surface. Fusion to the amino terminal region of the pilin protein is preferred.

Successful display of the target protein on the cell surface can be detected using a number of methods, for example, if the target peptide can be specifically labelled by a procedure that does not operate through the membrane, its cell surface display can be readily demonstrated. This can be done by iodination ($^{125}$I) of tyrosyl residues in the presence of lactoperoxidase [Marchalonis, et al., *J. Biochem.*, 124:921–927 (1971); King and Swanson, *Infect. Immunol.*, 21:575–584 (1978)].

In addition, one can examine if the target polypeptide is accessible to proteases added from the outside to intact cells. The action of the protease can be monitored by looking at the cleavage of the polypeptide by SDS-PAGE, or by examining if other properties of the polypeptide are affected (enzyme activity, antigenicity, etc.).

If the target polypeptide displays enzymatic activity, one may use such activity to demonstrate cell surface display. This can be done if a substrate unable to cross the outer membrane is available: nitrocefin is such a substrate for β-lactamase [O'Callaghan, et al., *Res. Microbiol.*, 141:963–969 (1972); Kornacker and Pugsley, *Mol. Microbiol.*, 4(7):1101–1109 (1990)]. It is important to ensure that the outer membrane is indeed impermeable to the substrate when the hybrid protein is expressed.

Antibodies against the target protein may also be used. However, these methods have limitations. First, the fusion protein may be constrained in conformation where the target polypeptide is not detected by the antibody used [Charbit, et al., Embo, J., 5:3029–3037 (1986); MacIntyre, et al., *J. Biol. Chem.*, 263:19053–19059 (1988)]. Second, if the antibody is targeted to a short peptide within the target (for example, an epitope included within 10 residues), the results will only give information on this epitope; thus a positive result may indicate that only this short peptide is exposed, whereas a negative result may indicate that part of the epitope is not accessible, which does not mean that some other part of the target protein is not exposed.

Binding of the antibodies to the bacteria can be examined with a number of different techniques. Such methods include, bacterial agglutination, immunofluorescence, ELISA with intact cells, RIA with intact cells, immunoelectron microscopy, and targeted action of complement [see, M. Hofning, *Methods in Cell Biology*, 34:77 (1991)].

The chimeric DNA may be integrated into the host cell chromosome or be carried within a vector. Methods of integrating DNA into a host cell chromosome are well known in the art and include, for example, homologous recombination. See, Winona, et al. *J. Bacteriol* 161:219–21 (1985). The chimeric DNA may also be carried within a recombinant vector, e.g., a plasmid. Recombinant vectors are preferred.

The recombinant vectors of the present invention comprise a vector backbone and the chimeric DNA. The recombinant vectors may include an inducible promoter sequence operably linked to the chimeric DNA. Promoters are well known in the art and can readily be selected depending on what cell type is to be used for expression of the fusion protein. The DNA segment encoding the leader is preferably positioned downstream of the promoter sequence. The traA leader sequence is preferred. The DNA segment encoding the target peptide is positioned downstream of the leader sequence. The DNA segment encoding the traA gene product is preferably positioned downstream of the DNA encoding the target peptide.

Plasmids useful as the vector backbone include plasmids containing replicon and control sequences which are derived from species compatible with the host cell. For example, if *E. coli* is used as a host cell, plasmids such as pUC19, pUC18 or pBR322 may be used.

Vectors can also be constructed comprising the traA leader DNA segments and the traA DNA segment with a cloning site incorporated between the DNA segments to allow insertion of DNA encoding a target protein or insertion of a DNA library. The vector may also contain an inducible promoter and marker gene, e.g., antibiotic resistance.

A preferred recombinant vector of the present invention is plasmid pPR35. This plasmid contains a traA leader DNA segment and a traA DNA segment downstream of the inducible lacZ promoter of pUC19. Cloning sites for NcoI, SfiI and NotI are incorporated between the traA leader and traA protein sequences to allow insertion of the DNA segments encoding the target peptide. In addition, a DNA sequence encoding the EE tag antigen is positioned between the traA leader and traA protein sequences to allow for detection of the fusion protein and characterization of the expression-display system, Introduction of the chimeric DNA to the host cell may be effected by any method known to those skilled in the art. For example, if the DNA is carried by a recombinant vector, the vector can be introduced, for example, by transformation, electroporation, or phage transfection.

The detection techniques noted above can be used initially to verify that the method of the present invention is working, i.e., that the fusion pilin protein has been expressed and transported to the bacterial cell surface and is orientated so that the target protein is accessible i.e., displayed.

Cells that display the target may be separated from those which do not, using, for example, affinity separation techniques. Such techniques include affinity column chromatography, batch elution from affinity matrix material and fluorescent-activated cell sorting.

A bacterial display library produced in accordance with the present invention can be separated by affinity chromatography just as with the phage. Because bacterial cells are larger, care must be taken during loading to prevent plugging and the non-specific retention of bacteria in the column. Subsequently, the cells can be eluted either by passing free antigen through the column or by low pH. Even though gram-negative bacteria are not as resistant to low pH as are phage, there is no meaningful decrease in cell vitality for at least 10 minutes at pH 3.3 [Martineul, et al., *Bio/Technology*, 9:170 (1991)]. Thus, elution by low pH and rapid neutralization can be employed for the isolation of strong binding clones.

The host cells displaying the desired target protein (display bacteria) may then be further cultured and used to obtain the fusion protein. If desired, the target protein may be separated from the pilin protein and further purified using pilin purification techniques familiar to the artisan [*J. Bacteriology*, 146(1):251–259 (1981)].

Once a desired target protein has been displayed, one can mutate the DNA encoding the heterologous polypeptide, e.g., by use of a mutator strain, and use affinity separation technology to identify and select peptides that bind to one or more targets.

The display method of the present invention can be used for the detection and characterization of recombinant proteins. For example, the method can be used to map an uncharacterized epitope as follows: Sequences encoding either a library of (1) random peptides or (2) peptides derived from the immunoreactive protein of interest can be cloned into a traA expression vector of the present invention, e.g., pPR35. E. coli host cells capable of forming F pili (e.g. XL1B) are then transformed with the vector bank and the peptide library-traA fusion proteins are displayed on the bacterial cell surface. Following growth on a solid substrate, e.g., a nylon membrane, the resulting bacteria are screened for expression of the fusion protein that react with labeled antibody. Reactive colonies can then be picked and the vectors isolated. Sequence analysis of the DNA insert would reveal which of the cloned peptides sequences corresponded to the epitopes recognized by the antibody.

The display method of the present invention can also be for detecting recombinant protein activity e.g., antibodies. For example, the method can readily be applied to screening libraries of recombinant antibody-traA fusion proteins. These libraries may include combinatorial single-chain gene banks of heavy and light variable region genes or mutational libraries of specific recombinant antibody genes [Reviewed in Whitlow, M & Filpula, D. (1991). Methods: A Companion to Methods in Enzymology 2:97–105.] On the basis of the results set forth in Examples 6 and 7 indicating that the α-CKMB scFv-traA fusion protein is folded into a biologically active conformation, this method has general application to detection of recombinant protein activities displayed on the surface of the bacterial cell colony. The activities to be detected could include binding activities, catalytic activities, inhibitory activities and altered structural conformations.

The present invention can also be used as a primary cloning system. For example, a cDNA library can be constructed and inserted in a vector of the present invention and the library screened for the ability to bind a ligand. The ligand/binding molecule combination could include any pair of molecules with an ability to specifically bind to one another, e.g., receptor/ligand, enzyme/substrate (or analog), nucleic acid binding protein/nucleic acid, etc. If one member of the complementary pair is available, this may be a preferred way of isolating a clone for the other of the pair.

As discussed above, it will often be necessary to increase the diversity of a population of genes cloned for the display of their proteins on a bacterial surface or to mutate individual nucleotide sequence. In vitro or in vivo mutagenesis techniques can be used for either purpose and are well known to the skilled artisan. Alternatively, mutator strains can be used. A mutator strain is a strain which contains a genetic defect which causes DNA replicated with in it to be mutated with respect to its parent DNA. Such strains include those carrying the rout D5 mutation such as ES 1578. Therefore, if a population of genes is introduced into these strains, it will be further diversified and can be transferred to a non-mutator strain if desired, for display and selection.

Since the F pili acts a receptor for the RNA bacteriophage and filamentous DNA phage, the display method of the present invention can make use of a binding protein on the phage to target the phage genome to a particular bacterial cell displaying a protein recognized by the phage. For example, instead of having the pilus/bacteriophage interaction that allows the phage to enter the cell, an antigen/antibody interaction can be used to allow the bacteriophage to interact with the pili and then enter the cell. For filamentous phage, the product of gene III acts as the attachment protein, it is believed, through interactions with residues near the N-terminus of the pilin protein. The gene III protein is made up of specific domains involved in incorporation into the page coat, phage morphology, interactions with the bacteria pilus, and entry into the bacteria cells, as depicted in FIG. 10.

In addition to filamentous bacteriophage, RNA bacteriophage, such as Qβ, MS2, f2 and R17, specifically interact with the F pilus and infect the cells. The ability to absorb to the pilus is conferred by maturation A protein (or $A_2$ for Qβ) which is present in one copy per virion [Paranchych, W. (1975) in RNA Phages, ed. N. D. Zinder. (Cold Spring Harbor Laboratory:New York). pp.85–112]. Like the gene III protein of filamentous bacteriophage, the RNA phage maturation A protein can be used to form fusions without affecting infectivity.

In accordance with this method, a display bacteria is formed in which one protein of the specific binding pair is displayed and replaces the natural receptor for bacteriophage infection. A bacteriophage is also altered such that the normal pilin interaction domain is substituted with the other member of the specific binding pair. This is accomplished by removing the region of the phage attachment protein (e.g. gene III protein of filamentous phage or the A protein of RNA phage) that encodes the pilin binding domain and inserting in its place DNA that encodes the second member of the specific binding pair. The chimeric gene may be incorporated into the phage genome or a recombinant phagemid expression vector. The gene is then expressed in the appropriate strain, e.g. E. coli, and the fusion protein and the corresponding phage (or phagemid) genome are packaged into the bacteriophage particles. The phage is then contacted with the display bacteria under standard conditions. Phage displaying one member of the specific binding pair recognize and infect the bacteria displaying the other member based on the protein-protein interactions between the displayed proteins. The phage genome is then internalized by the display bacteria. Display bacteria infected with the phage genome can then be selected by, for example, identifying of a marker gene i.e., antibiotic resistance, transferred from the phage to the display bacteria. DNA encoding members of the specific binding pair can then be isolated from the display bacterial host.

Using fd phage, for example, the phage is altered such that the normal pilin interaction domain (e.g., amino acid 107 to 197 of the gene III protein) is removed and replaced by a polypeptide which will specifically bind the target protein displayed on the display bacteria. Thus, the display phage recognizes and infects the display bacteria solely based on the protein-protein interactions between the displayed recombinant proteins. FIG. 11 shows the general characteristics of this system. The phage or phagemid genome is then internalized and expressed. Control signals for transcription, translation and replication can be present. It is particularly useful if the phage or phagemid genome contain sequences useful in selecting for the desired target cell. Useful sequences include, for example, those conferring antibiotic resistance to the target cell.

Bacteriophage useful in the method of the present invention include filamentous phage and RNA phage that utilize as a receptor the pilin protein. Such phage include MS2, Qβ, M13, f1, fd and fd-tet. In addition, phagemid expression vectors derived from such filamentous phage can also be used. These vectors can carry plasmid and phage origins of replication and genes that confer antibiotic resistance. The preferred phage is fd-tet [Zacher, A. N., Stock, C. A., Golden, J. W. and Smith, G. P. (1980) Gene 9, 127–140] and the preferred phagemid is a derivative of f1 phage such as pBC (Stratagene).

As an example of this method, the EE tag antigen is displayed on the bacteria pili as a traA fusion using a phagemid expression vector that has been developed to allow for recombinant proteins to be displayed on the surface of bacteriophage. Using this system, the anti-EE tag scFv is displayed on the surface of the bacteriophage particles as a fusion with the gene III protein that has the pilin binding region (amino acid 107–197) deleted (this protein will be referred to as geneIIIp ΔBS as shown in FIG. 10). Interactions between the anti-EE tag scFv antibody and the EE tag antigen are measured by the ability of the display phage to infect the display bacteria. Specific strategies for generating the display bacteriophage and for measuring infection are set out in Example 8 below.

Other recombinant proteins can be displayed on the bacteriophage and bacterial cell surface. These can include libraries of scFv genes displayed on the phage and a specific antigen peptide on the display bacteria. Screening for specific scFv-antigen interactions involves 1) rescue of the scFv display phagemid particles and 2) mixing the phage with the antigen displaying bacteria and testing for the presence of a marker e.g., infectivity by growth on agar plates containing antibiotics (chloramphenicol). The method of the present invention does not require antigen purification or the multiple rounds of enrichment and phage amplification steps that are currently required in phage display systems.

Phage or phagemid DNA would be isolated from the resulting antibiotic resistant colonies and the candidate scFv genes could be sequenced. Once the initial characterization is completed, the candidate scFv genes could be subcloned into bacteria expression vectors for the production and further characterization of the single-chain antibodies.

A bacteriophage vector based system can also be constructed for display of the recombinant proteins. Such a method has the advantages that it can be used to genetically select for high affinity protein-protein interactions and for binding affinity improvement when coupled with random or site-directed mutagenesis of the recombinant protein. As an example, an expression vector is constructed from the fd-tet phage by replacing the normal geneIII with the anti-EE tag scFv-geneIIIp ΔBS fusion gene as outlined in FIG. 13. DH5-αF' cells are transformed to tetracycline resistance with the phage expression vector. The transformed cells are be grown overnight, for example, in 100 ml of 2×YT media containing 15 μg/ml tetracycline. The cells are removed by centrifugation and the phage particles in the culture media can be concentrated by precipitation with, for example, 5% PEG and 0.5M NaCl. The resulting phage particles carry the geneIIIp ΔBS phage vector and display the anti-EE tag scFv-geneIIIp ΔBS fusion protein of the bacteriophage surface. These phage particles are used to infect DH5-αF' cells carrying the EE tag-traA fusion vector. Infectivity can be tested by selection of tetracycline resistant colonies on agar plates as previously described. Alternatively, since the expression phage is able to replicate and re-infect bacteria displaying the EE tag, infectivity can be characterized by the formation of plaques on a lawn of the display bacteria or the propagation of the phage is liquid cultures of the display bacteria. Plaque size or phage titer liquid media provides an indication of the strength of the recombinant protein-protein interactions responsible for the phage infectivity and propagation. In other words, the highest affinity recombinant protein-protein interactions between the display phage and the display bacteria results the highest infectivity rates. The specificity of the infection can be tested with cells that do not display the EE tag antigen.

This system is useful in screening libraries of recombinant protein such as scFv. Phage displaying the high affinity scFv can infect and replicate in the antigen displaying bacteria at a higher rates than the phage displaying low affinity scFv. Thus, the phage displaying the high affinity scFv will be selectively enriched with continued growth of the culture. This is true for other specific binding pairs as well. The resulting phage DNA can be isolated and the candidate scFv genes and proteins further characterized by sequence and affinity analyses.

This system can further be used to screen compounds, i.e., inhibitors or co-factors, that affect specific binding pair interaction. In this screening method, the display bacteria and the display phage are mixed and infectivity of the display phage or phagemid particles is measured as previously described. One such detection method would be antibiotic-resistant growth of the display bacteria following infection with the display phage carrying the antibiotic resistance gene. Candidate compounds are added to the binding reaction and the effect on the level of phage infectivity is measured. For example, the suppression of growth of the display bacteria in appropriate selective media is one means of screening a large number of candidate inhibitor molecules. Compounds potentiating binding can be selected by screening for increased growth.

The present invention is further illustrated by the following Examples. These Examples are provided to aid in the understanding of the invention and are not construed as a limitation thereof.

The references cited above and below are herein incorporated by reference.

EXAMPLE 1

CONSTRUCTION OF A traA FUSION VECTOR FOR EXPRESSING PROTEINS ON THE BACTERIAL SURFACE A system was designed to allow inducible expression and display of polypeptides fused to the amino terminus of the pilin protein on the surface of bacteria. In this system, the gene encoding the polypeptide of interest was cloned into the traA vector, pPR35 and expressed in an F⁺ bacteria strain. The traA expression vector is based on the multicopy pUC19 vector with features shown in FIG. 1. The traA leader and traA protein (pilin) DNA fragments were cloned downstream of the inducible lacZ promoter of pUC19. The traA leader allows for proper processing and display of the pilin fusion protein. Cloning sites for NcoI, SfiI and NotI were incorporated between the traA leader and pilin polypeptide sequences to allow insertion of foreign DNA sequences. In addition, a DNA sequence encoding the EE tag antigen was cloned between the traA leader and traA protein sequences to allow for detection of the fusion protein and characterization of the expression-display system.

Figure 2:
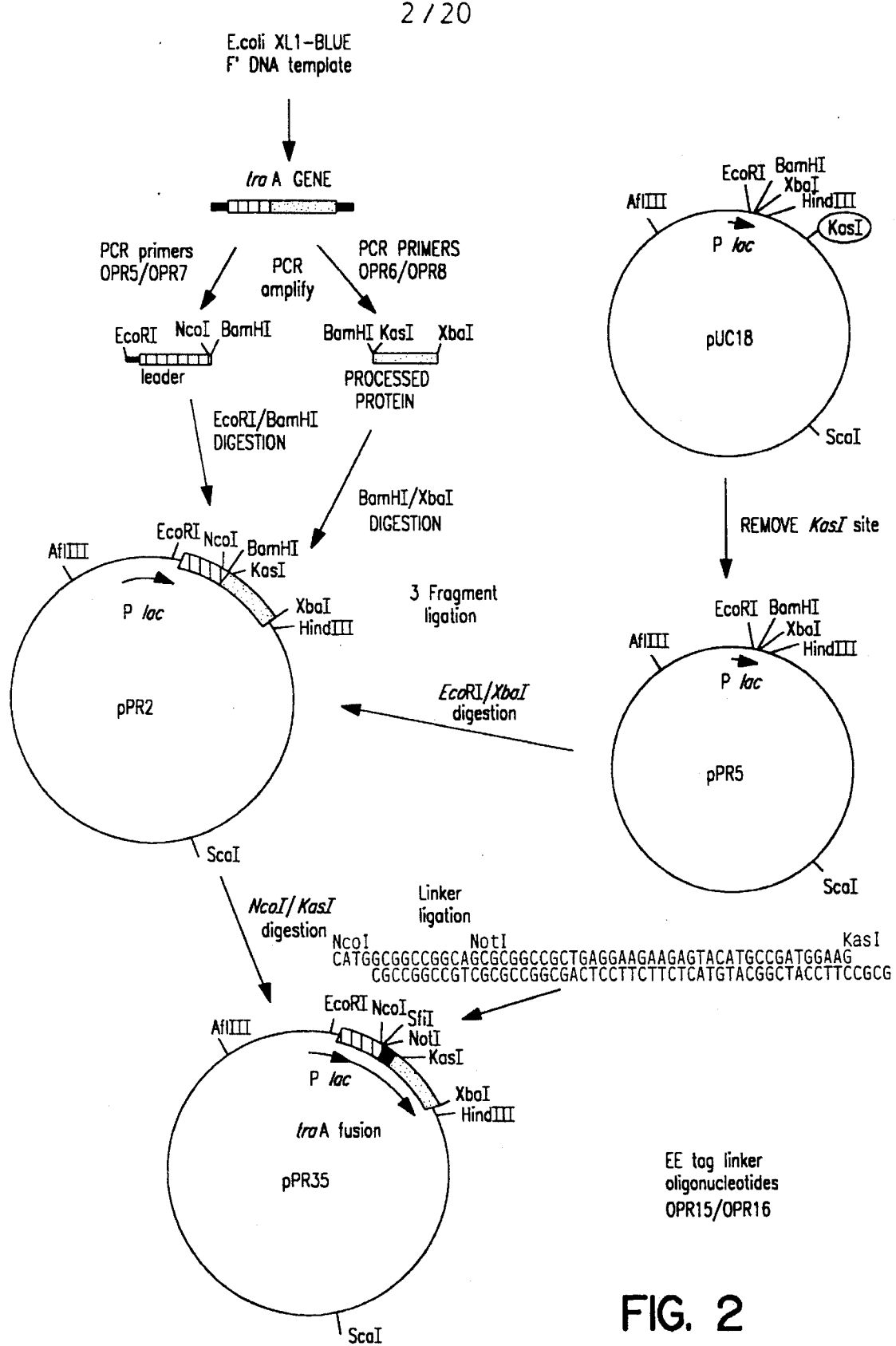
FIG. 2 sets forth the construction of pPR35 (OPR15 has SEQ ID NO: 15; OPR16 has SEQ ID NO: 16).

The steps required to construct the pPR35 vector are outlined in FIG. 2 and detailed as follows. The traA leader and traA protein gene fragments were amplified separately by PCR from an F plasmid template. The primers used in the amplification are described in FIG. 2 and FIG. 3. Typical PCR amplification reactions (100 μl) contained $10^5$ boiled XL1B bacteria cells carrying the F plasmid as source of template DNA, 10 pmoles of the appropriate primers, 2.5 units of Taq polymerase, 100 μM dNTP, 50 mM KCl, 10 mM Tris-HCl, pH 8.3, 1.5 mM $MgCl_2$, 0.01% gelatin. The template was denatured by an initial incubation at 96° C. for 5 min. during which the Taq polymerase was added to hot-start the reaction. The desired products were amplified by 10 thermal cycles of 55° C. for 1 min., 70° C. for 1 min. and 96° C. for 1 min. followed by 20-step cycles of 70° C. for 1 min. and 96° C. for 1 min. Amplification with the primers results in the addition of an EcoRI site on the 5' end of NcoI and BalI sites on the 3' end of the traA leader fragment and BamHI and KasI sites on the 5' end and an XbaI site on the 3' end of the traA protein fragment. The PCR products from 5 reactions were pooled, precipitated with 2 volumes of ethanol/0.3M sodium acetate, and the resulting products (about 0.2 μg of DNA) were resuspended in water. The traA leader PCR product was digested with EcoRI and BamHI and the traA protein PCR fragment was digested with BamHI and XbaI. The digested fragments were resolved by agarose gel electrophoresis and purified by elution from the agarose gel. In order to clone these fragments, a vector referred to as pPR5 was generated by digesting pUS18 DNA with KasI, filling-in the site with Klenow DNA polymerase and religating the blunt ends. The purified digested PCR products were then ligated into EcoRI/XbaI digested pPR5. Bacteria transformed with this ligation mix were screened for the product of the three fragment ligation. Shown in FIG. 2, this vector is referred to as pPR2. Finally, the EE tag linker sequence was generated by two complementary oligonucleotide which was annealed have a NcoI sticky end at the 5' end and a KasI sticky end at the 3' end. The annealed oligonucleotide were ligated into NcoI/KasI digested pPR2 to give the traA fusion vector, pPR35. The sequence of pPR35 is shown in FIG. 4.

EXAMPLE 2

ISOLATION OF SINGLE-CHAIN ANTIBODY GENE AND CLONING INTO THE traA FUSION VECTOR

Figure 5A:
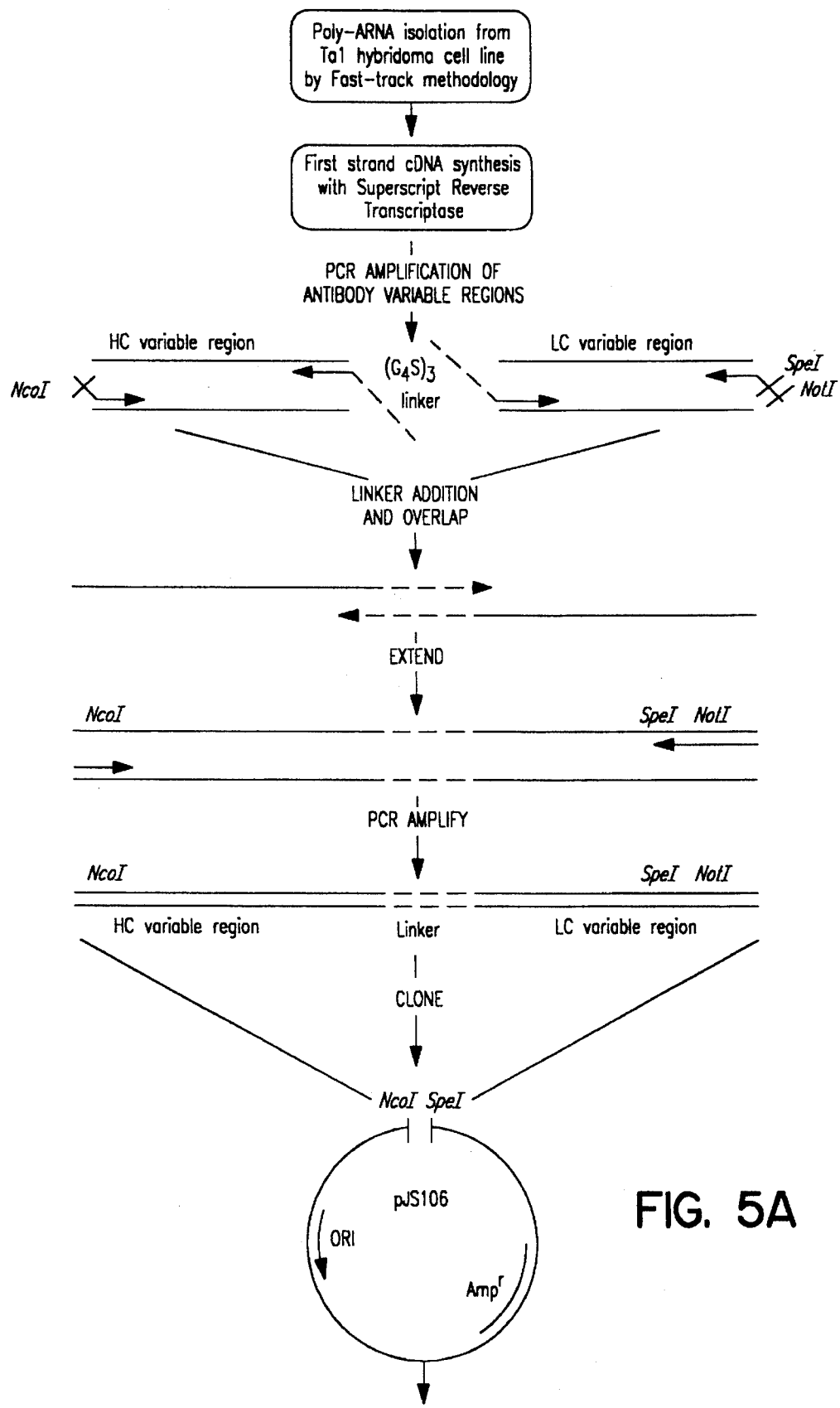
FIGS. 5A and 5B set forth the construction of pGH21.
Figure 5B:
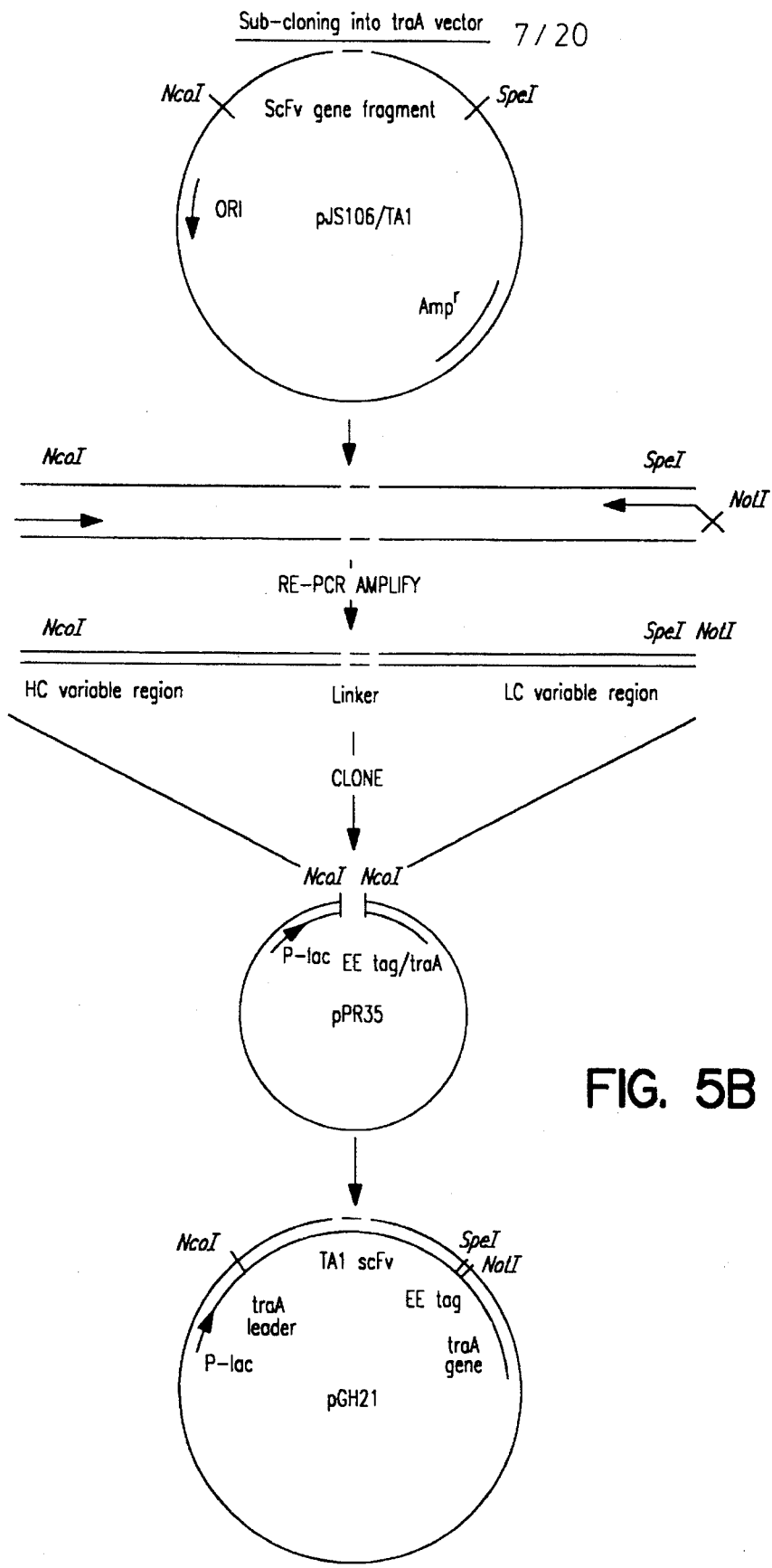

The traA fusion vector has been designed to express both peptide antigens such as the EE antigen as well as other recombinant proteins such as single chain antibodies. For the purpose of this example, single-chain antibody genes were created in which the heavy and light variable regions of a particular monoclonal antibody were joined together by a flexible polypeptides linker. Single-chain antibody (scFv) genes were generated from a monoclonal antibody (TA1) directed against the prothrombin polypeptide F1.2 and from a monoclonal antibody directed against creatine kinase-MB (α-CKMB) as described below and outlined in FIG. 5. For the TA1-ScFv, the first step involved poly-A RNA isolation from TA1 hybridoma cells by using the Fast-track RNA isolation kit (Invitrogen) according to manufacturer's procedures. This RNA (1/10 of the mRNA isolated was used) was converted to cDNA using Superscript-MLV Reverse Transcriptase (GIBCO-BRL) and oligo-dT specific priming according to manufacturer's procedures. Of the 20 μl of cDNA generated, 2 μl was used as template DNA for PCR. The PCR primers for amplifying the TA1 mAb heavy and light chain variable region genes are JS135/JS134 and JS133/JS153, respectively, as shown in FIG. 2. The PCR buffer conditions are the same as described in Example 1. The template was denatured by an initial incubation at 96° C. for 5 min. during which the Taq polymerase was added to hot-start the reaction. The immunoglobulin variable region gene fragments were amplified by 10 thermal cycles of 48° C. for 1 min., 70° C. for 1 min., and 96° C. for 1 min. followed by 25-step cycles of 70° C. for 1 min. and 96° C. for 1 min. The desired products (about 260 bp) were resolved by agarose gel electrophoresis and purified by elution from the agarose gel. These fragments were then used as DNA templates in PCRs to attach a 45 nucleotide linker sequence to the 3' end of the heavy chain and the 5' end of the light chain variable gene fragment, resulting in the addition of a flexible 15 amino acid peptide linker to the variable region polypeptides. The PCR primers used in the linker attachment are JS135/JS139 and JS137/JS153 for the heavy and light chain variable gene fragments, respectively. The PCR conditions were 10 thermal cycles of 48° C. for 1 min., 70° C. for 1 min., and 96° C. for 1 min., followed by 25-step cycles of 70° C. for 1 min., and 96° C. for 1 min. Following resolution by agarose gel electrophoresis, the desired products (about 400 bp) purified by elution from the agarose gel. Sequence-overlap extension PCR was used to link the heavy and light chain variable gene fragments by first annealing and extending the heavy chain+light chain variable+linker gene fragments for 10 thermal cycles of 52° C. for 1 min., 70° C. for 1 min., and 96° C. for 1 min. The linked fragments were then amplified by the addition of JS135/JS153 primers and 15 additional step cycles of 70° C. for 1 min. and 96° C. for 1 min. The desired products (about 720 bp) were purified as described above. Initially, the TA1 scFv gene fragment was digested with NcoI and SpeI and ligated into the pJS102 cloning vector digested with NcoI/SpeI. The resulting construct was sequenced to verify that it contains the TA1 scFv gene. The pJS102/TA1 scFv plasmid was then used as template DNA to PCR the TA1 scFv gene fragment in order to add a NotI site to the 3' end of the light chain variable gene. The primers used were JS135/JS153 and the PCR conditions were 10 thermal cycles of 48° C. for 1 min., 70° C. for 1 min. and 96° C. for 1 min. followed by 25-step cycles of 70° C. for 1 min. and 96° C. for 1 min. The desired products (about 720 bp) were resolved by agarose gel electrophoresis and purified by elution from agarose gel. The TA1 scFv gene fragments were digested with NcoI and NotI and ligated into the pPR35 traA expression vector digested with NcoI/NotI, resulting the creation of the TA1 scFv/EE tag/traA fusion vector, pGH21.

The same strategy was used to isolate the variable region genes from Conan α-CKMB hybridoma cell line and to construct the α-CKMB scFv gene. The corresponding heavy and light chain PCR primers are shown in FIG. 3. Following the sequence-overlap expression PCR step, the α-CKMB scFv gene fragment was digested NcoI and SpeI and ligated into the pGH21 traA expression vector digested with NcoI/SpeI, essentially swapping the TA1 scFv gene for the α-CKMB scFv gene. The resulting construct is referred to as pα-CKMB scFv-traA.

EXAMPLE 3

PRODUCTION OF traA FUSION PROTEINS

The traA expression system was characterized in several ways. First, bacterial expression of the TA1 scFv-EE tag-traA or α-CKMB scFv-EE tag-traA fusion protein was examined by immunoblot analysis. The pGH21 and pα-CKMB scFv-traA vectors were transformed into XL1B cells carrying the F plasmid. Correct candidates were screened by restriction analysis of alkaline-SDS miniprep DNA and verified by DNA sequencing. To induce the expression of the traA fusion protein, 60 μl of an overnight culture was used to inoculate 3 ml of 2×LB media, 50 μg/ml ampicillin, 15 μg/ml tetracycline. Following a 2 hour incubation at 37° C., isopropyl-1-thio β-D-galactoside (IPTG) was added to 2 mM final concentration. After 4 hours at 37° C., the $OD_{600}$ of the culture was determined and 2 ml of the culture was harvested by microcentrifugation for 5 min. The cell pellet was frozen at −70° C. and then was resuspended at 10 ODs/ml in cold TxTBS (0.1% Triton C-100, 10 mM Tris-HCl, pH 7.4, 0.15M NaCl). The cells were sonicated for 3 to 5 min. and the cell debris removed by microcentrifugation at 10,000×g for 10 min. at 4° C. The supernatant (10 μl) was mixed with SDS//β-mercaptoethanol loading buffer and boiled for 5 min. to denature the proteins. The samples were resolved by SDS-polyacrylamide gel electrophoresis on 12.5% polyacrylamide gels. The material in the gels was transferred to PVDF nylon membranes using a semi-dry transblot apparatus. The membrane was blocked overnight at 4° C. with 20 ml of blocking buffer (0.5% NP-40, 0.5% non-fat dried milk in PBS) and probed with 20 ml of 43 ng/ml anti-EE tag mAb conjugated to horseradish preoxidase (anti-EE tag mAb-HRP). The anti-EE tag mAb-HRP was detected by the ECL reagent (Amersham). The signal for the α-CKMB scFv-traA fusion protein was detected at the expected molecular weight of 40 kD, while lysates from XL1B/vector alone showed no signal. The TA1 scFv-traA fusion protein migrates at 46 kD, however, the TA1 scFv protein migrates through SDS-PA gels at a higher molecular weight than expected. The TA1 scFv-traA fusion protein was also detected in the growth media, consistent with the fact that F pili can detach from the cell surface and be found in the media.

Figure 15:
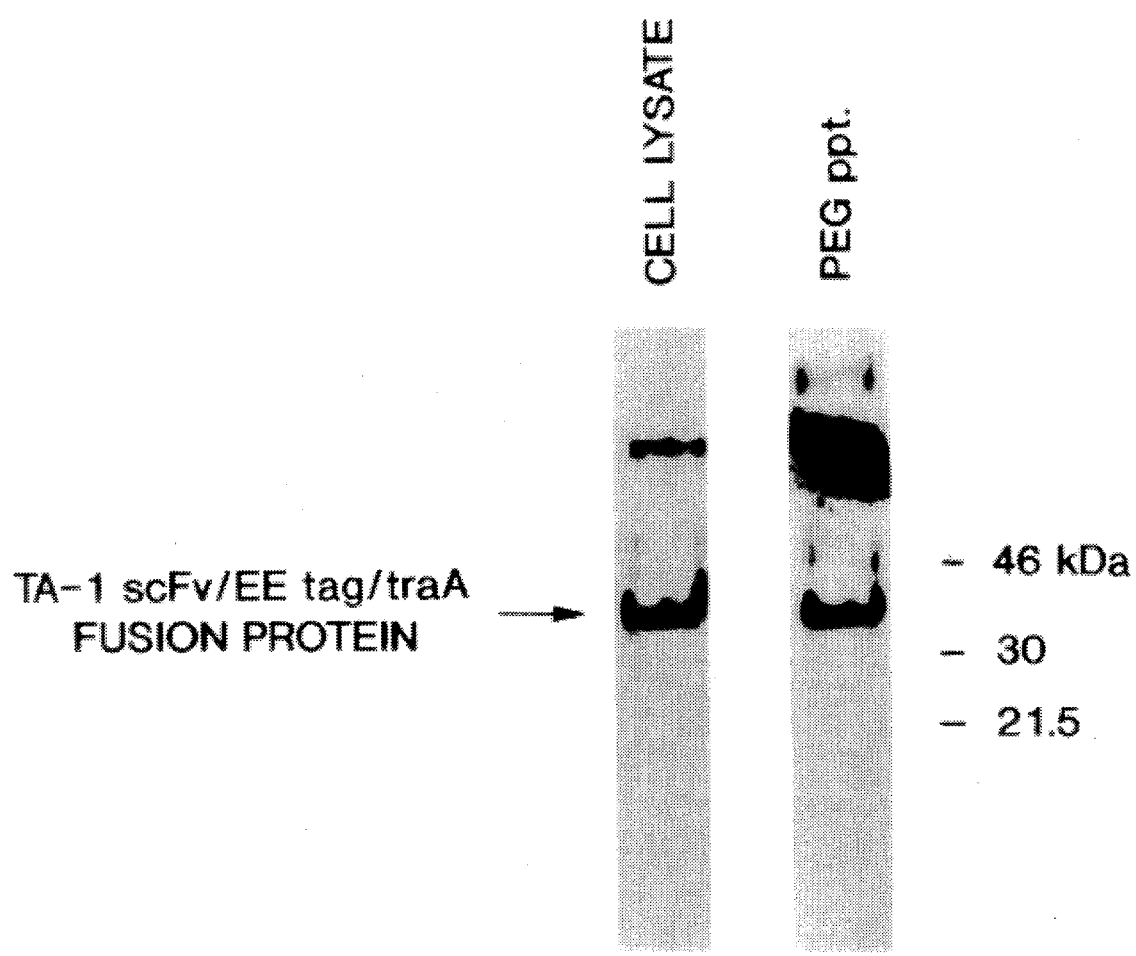
FIG. 15 shows a Western blot analysis of partially purified TA-1 scFv/EE tag/traA fusion protein. XL1-B/pGH21 cells (1 L) were grown and TA-1/EE tag/traA fusion protein expression was induced with IPTG as described in example 2. The bacteria pilin protein was partially purified by shearing the pili from the cells and PEG precipitation as described by Moore et al. (J. Bacteriology, 146 (1):251–259, 1981). The fusion proteins present in the induced cells (cell lysate lane) and in the partially purified protein (PEG ppt. lane) were examined by western analysis using the anti-EE tag mAb-HRP as a probe. The band corresponding to the TA-1/EE tag/traA fusion protein is indicated. The immunoreactive material at the top of the stacking gel is aggregated fusion protein that does not enter the resolving gel.

XL1-B/pGH21 cells (1L) were grown and TA-1/EE tag/traA fusion protein expression was induced with IPTG as described in Example 2. The bacteria pilin protein was partially purified by shearing the pili from the cells and PEG precipitation as described by Moore, et al. [*J. Bacteriology*, 146(1):251–259 (1981)]. The fusion proteins present in the induced cells (cell lysate lane) and in the partially purified protein (PEG ppt lane) were examined by Western analysis using the anti-EE tag mAb-HRP as a probe. See, FIG. 15. The band corresponding to the TA-1/EE tag/traA fusion protein is indicated. The immunoreactive material at the top of the stacking gel is aggregated fusion protein that does not enter the resolving gel.

EXAMPLE 4

DETECTION OF THE ANTIGEN-traA FUSION PROTEIN ON THE BACTERIAL SURFACE BY CLONING SCREENING The traA expression system was used to develop improved methods for the detection of recombinant proteins. Two simple detection methods were performed to test whether the antigen-traA fusion protein was displayed on the surface of the bacteria cells. The first was an immunodetection method for screening for bacterial colonies grown on nylon membranes. The XL1B strain expressing the TA1-EE tag-traA fusion protein was spread on a nylon membrane and the membrane was placed on 2×LB agar plate containing 50 μg/ml ampicillin and 15 μg/ml tetracycline for selection of the vector and XL1B strain, respectively. For induction of the traA fusion gene expression, the membrane was prewet with 10 mM IPTG. Following overnight incubation at 37° C., the membrane was removed from plate and washed 3 times by cold Imidazole buffer saline (IBS-40 mM Imidazole, pH 7.0, 0.15M NaCl). Membrane was blocked with 0.5% milk-PBS with agitation at 4° C. for 1 hour, and then incubated for 1 to 2 hours with 43 ng/ml anti-EE tag mAb-HRP in IBS at 4° C. Following 5 washes with IBS at 4° C., the membranes were reacted with ECL reagents and the immunoreactive material was detected. By this colony immunoblot methodology, anti-EE tag mAb-HRP recognized the IPTG-induced XL1B/TA1-EE tag-traA colony but not the non-induced XL1B/TA1-EE tag-traA colony. XL1B cells carrying a control vector (no EE tag-traA) failed to give any signal. The specificity of binding of anti-EE tag mAb on cell surface was also determined by incubating the colony membrane with an antibody to a different peptide tag (KT3). No signal was detected on these membranes.

Figure 6:
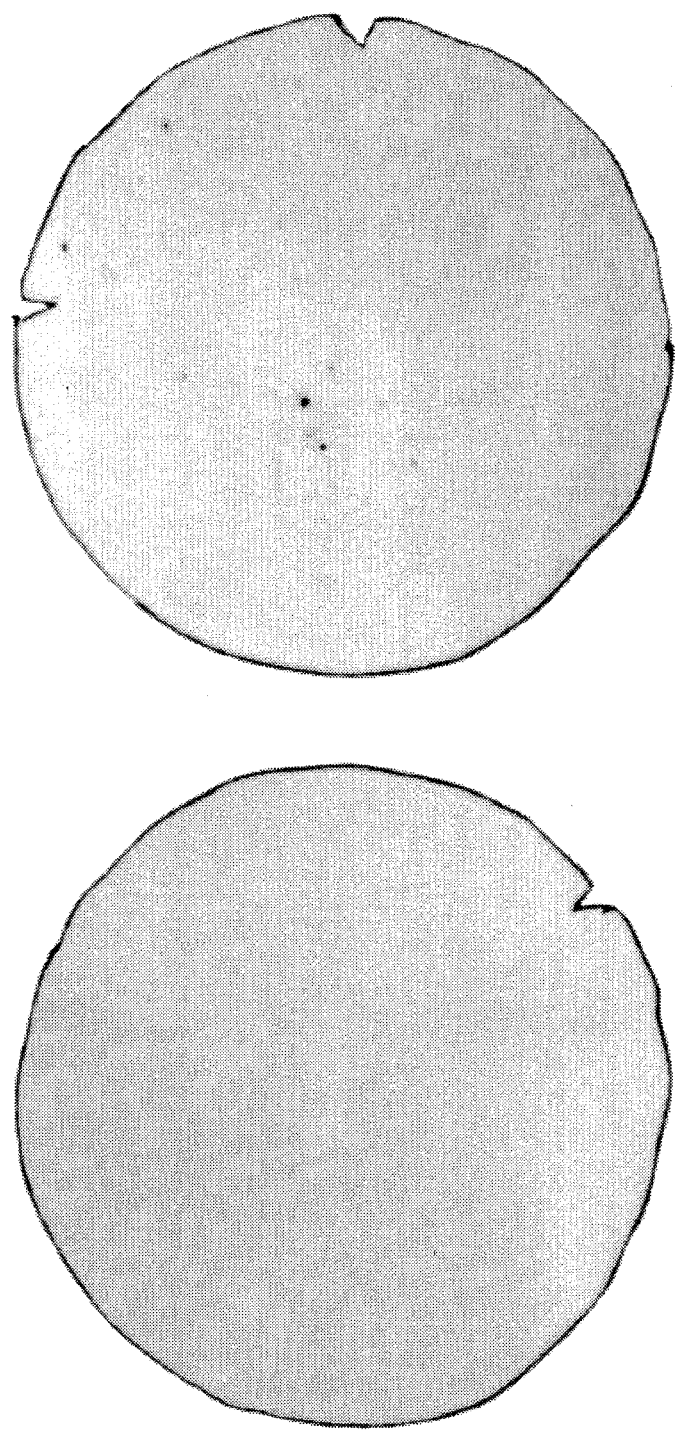
FIG. 6 demonstrates the detection of antigen on the surface of a bacterial host cell by colony immunoblotting.

The bacteria colony immunodetection method was also applied to epitope mapping analysis. To test this method, mixtures of XL1B cells carrying either the TA1-EE tag-traA or the control vector (no EE tag-traA insert) were grown overnight on 2×LB agar plates containing 50 μg/ml ampicillin and 15 μg/ml tetracycline overnight. The colonies were replica-plated onto nylon membranes and placed on 2×LB agar plates containing 10 mM IPTG, 50 μg/ml ampicillin and 15 μg/ml tetracycline. Following growth at 37° C., the colonies on the membranes were probed with anti-EE tag mAb-HRP as described above. In the IPTG induced samples, positive signals were detected for single colonies as shown in FIG. 6. The corresponding colonies were picked from the master plate for characterization and were found to carrying the TA1-EE tag-traA vector.

EXAMPLE 5

WHOLE CELL ELISA TO DETECT ANTIGEN EXPRESSED ON THE BACTERIAL SURFACE

Figure 7:
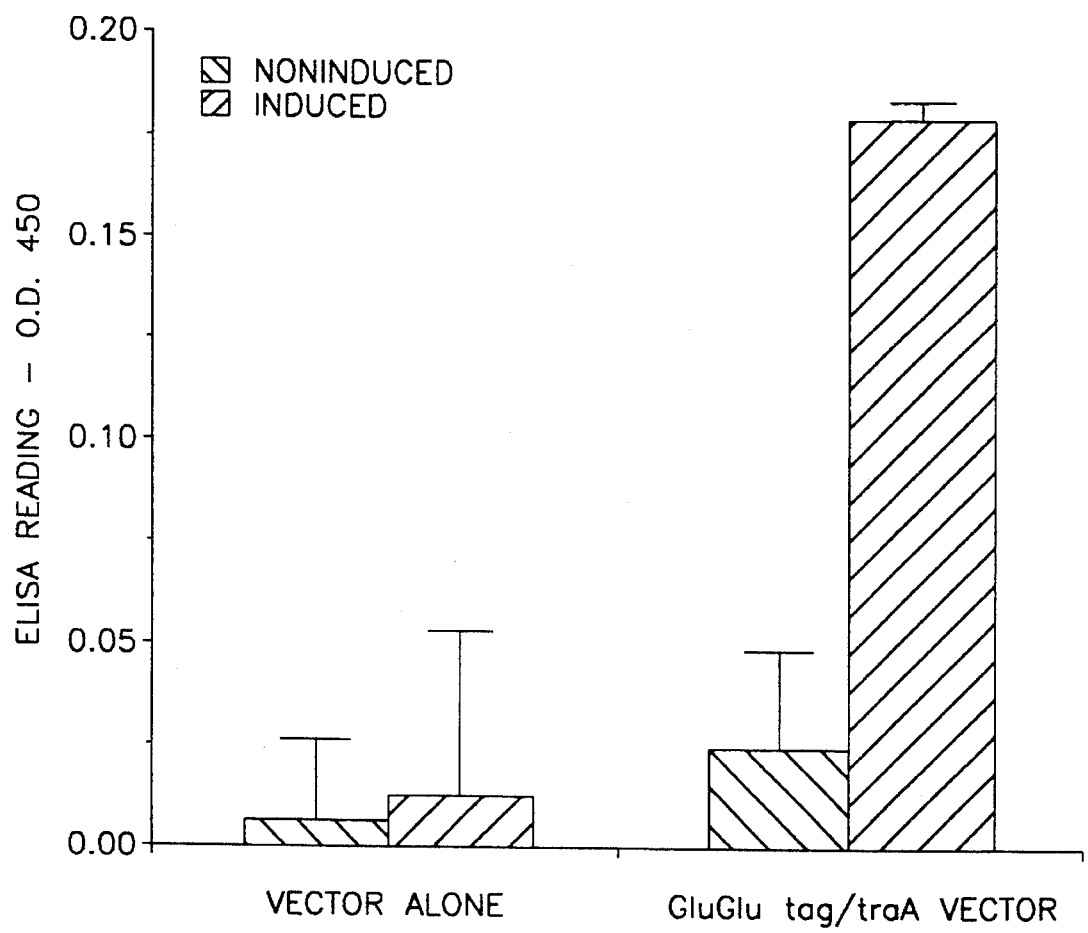
FIG. 7 is a graph demonstrating antigen tag expression on the cell surface.

The second method to test the accessibility of the antigen-traA fusion protein on the surface of the bacteria was an ELISA method with intact cells. Cell grown to early log-phase were induced by IPTG for 4 hours at 37° C. The cells were harvested and resuspended in cold PBS to 1.0 $OD_{595}$/ml. This step will remove any traA fusion protein present in the media that is not associated with the cells. Microtiter plates were coated with 100 μl of bacterial dilution per well. After overnight incubation at 4° C., unattached cells were discarded and wells were blocked with PBS containing 1% bovine serum albumin for 1 hour at 4° C. Following the blocking step, the wells were incubated with 100 μl of 0.34 μg/ml anti-EE tag antibody HRP. After 5 times washes with PBS, antigen-antibody complexes were developed by HRP-ELISA substrate ($H_2O_2$, ABTS peroxidaes substrate). Reaction values were recorded by ELISA reader. The $OD_{450}$ reading indicates the amount of anti-EE tag mAB-HRP activity captured in each well and correlates with the amount of EE tag fusion protein expressed on the cell surface. The induced XL1B/TA1-EE tag-traA samples showed greater than six-fold higher readings than the non-induced sample or the XL1B/control vector (no EE tag-traA insert) sample as shown in FIG. 7, indicating that this method is applicable to specifically detecting antigens presented on the cell surface. By adding known amounts of peptide antigen and antibody to the binding reaction, this method could be used to quantitative antibody/antigen binding. In addition, the epitope could be characterized in a comparative ELISA assay format where the effect of different peptides on antibody/antigen-traA fusion protein interaction is determined.

EXAMPLE 6

WHOLE CELL ELISA TO DETECT THE ACTIVITY OF A RECOMBINANT ANTIBODY DISPLAYED ON THE BACTERIAL SURFACE

Figure 8:
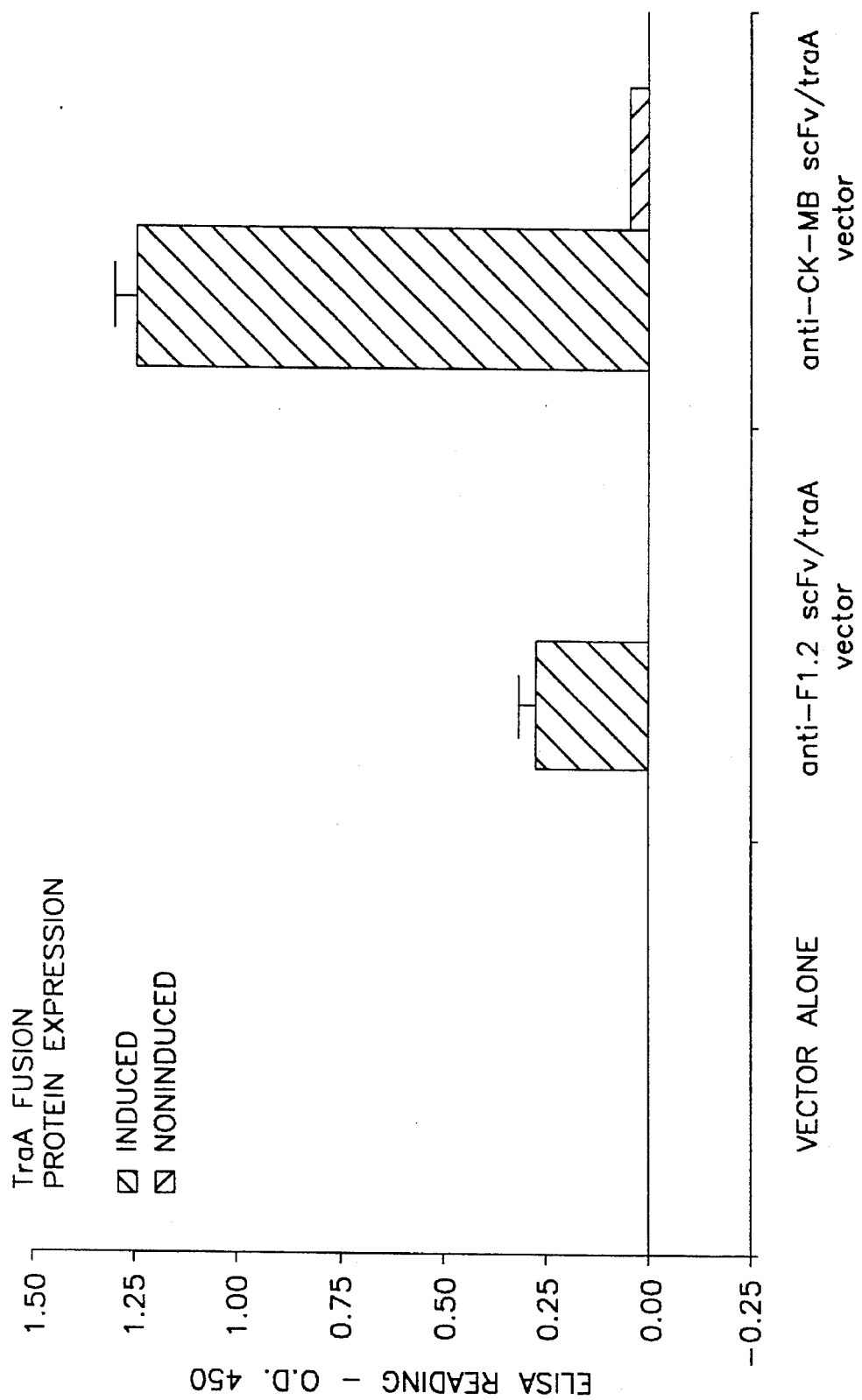
FIG. 8 is a graph demonstrating recombinant antibody expression on the cell surface.

The results from Examples 4 and 5 indicate that antigens fused to the traA protein could be displayed on the surface of bacteria and could be specifically detected by the corresponding antibody. Similar experiments were carried out to determine if a functional recombinant protein could be displayed of the bacterial surface as described below. To detect the activity of recombinant single chain anti-CKMB Ab displayed on the bacteria cell surface, an ELISA method with intact cells was performed. Cells carrying either the α-CKMB scFv-EE tag-traA fusion vector or the control vector (TA1-EE tag-traA fusion vector or a vector without an insert) were grown to early log-phase at 37° C. At that point, expression of the fusion protein was induced by the addition of 0.2 mM IPTG for 4 hours at 37° C. The cells were harvested and resuspended in cold PBS to 10.0 $OD_{595}$/ml. Microtiter plates were coated with 100 µg/ml anti-CK-BB mAb in coating buffer (0.1M Tris-HCl, pH8.5) and were incubated overnight at 4° C. Unattached anti-CK-BB mAb was discarded and the wells were washed once with washing buffer (0.1M Tris-HCl, pH 7.4, 1.0M NaCl, 0.1% $NAN_3$). The wells were incubated with 100 µl of 0.3 µg/ml CK-MB in dilution buffer (2% gelatin, 0.1% Tween 20 in 0.01 m Tris-HCl, pH7.3, 0.15M NaCl) at room temperature for 1 hour with agitation. The wells were washed once with rinse buffer (0.01M Tris-HCl, pH7.3, 0.15M NaCl, 0.2% BSA, 0.05% Tween-20, 0.2% $NaN_3$). 100 µl of cell suspension was added to each well and the plate was incubated at room temperature for 1 hour with agitation. The unattached cells were discarded and the wells were washed twice with rinse buffer. The wells were incubated with 100 µl of 0.34 µg/ml anti-EE tag mAb-HRP conjugate in dilution buffer at room temperature for 1 hour with agitation. After washing the wells twice with rinse buffer, the HRP-ELISA substrate ($H_2O_2$, ABTS peroxidase substrate) was added and developed for 20 min. The amount of color development as determined by an ELISA reader at 450 nm corresponds to the amount of scFv-EE tag-traA fusion protein detected in the well. These values correlate with the amount of anti-CKMB scFv activity displayed of the cell surface that is captured by the immobilized CK-MB. Typical results are shown in FIG. 8. The IPTG-induced XL1B/α-CKMB scFv-EE tag-traA plasmid sample showed 29-fold higher levels of captured α-CKMB scFv-EE tag-traA fusion protein than the non-induced XL1B/TA1-EE tag-traA cells that express a different recombinant antibody which does not recognize CK-MB. The XL1B cells carrying the control vector did not express EE tag-traA protein and showed no activity in this assay.

The results of these experiments indicate that the α-CKMB scFv domain of the fusion protein is folded into a biologically active conformation and is displayed on the surface of the cells. The combination of the single-chain antibody and the EE antigen tag on the same display protein allows for versatility in the development of ELISA formats. The sandwich capture ELISA format used in this Example is just one of the many possibilities.

EXAMPLE 7

DETECTION OF FUNCTIONAL SINGLE-CHAIN ACTIVITY OF THE BACTERIAL SURFACE BY COLONY SCREENING

Figure 9:
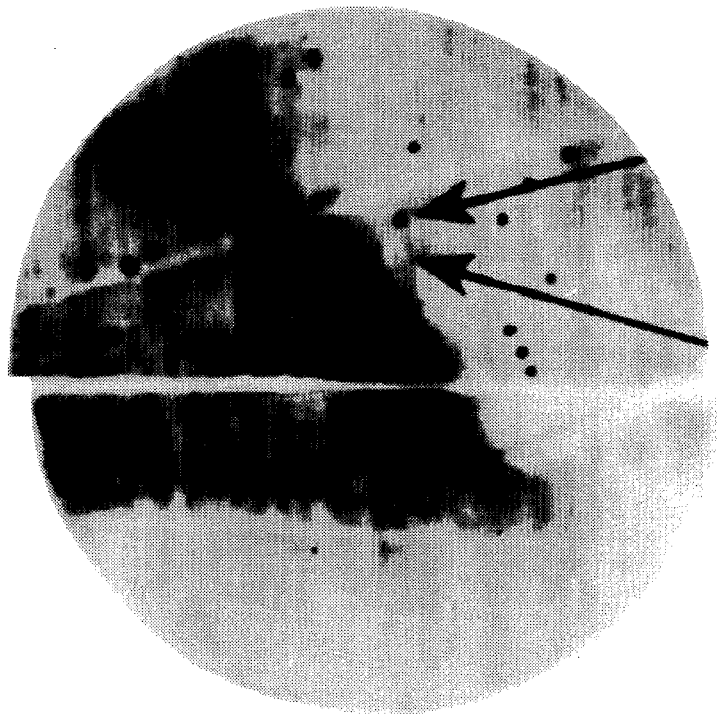
FIG. 9 is a colony blot showing detection of anti-CK-MB activity of the cell surface.

This example demonstrates the successful detection of a recombinant protein activity expressed on the surface of the bacterial cell colony. A mixture of the XL1B strain carrying the α-CKMB scFv-EE tag-traA fusion vector and the strain carrying the TA1-EE tag-traA fusion vector was distributed evenly on a nylon membrane. The membrane was placed on a 2×LB agar plate containing 50 µg/ml ampicillin and 15 µg/ml tetracycline and incubated at 37° C. until small bacterial colonies appeared. At this time, a replica membrane was made by overlaying the master membrane with a new membrane. The replica membrane was then removed and cut in half. One half was incubated on a 2×LB agar plate containing 10 mM IPTG, 50 µg/ml ampicillin and 15 µg/ml tetracycline and the other half was on a 2×LB agar plate containing just 50 µg/ml ampicillin and 15 µg/ml tetracycline. Following the overnight incubation at 37° C., the IPTG-induced and non-induced membranes were removed and washed 3 times by IBS. Membranes were blocked with 20 ml of 0.5% milk-IBS with agitation at 4° C. for 1 hour, and then incubated for 1 hour at 4° C. with 20 ml of 0.3 µg/ml CKMB in the dilution buffer. Following 3 washes with cold IBS, the membranes were blocked at 4° C. for 1 hour, and with anti-CK-BB mAb conjugated to alkaline phosphatase. Following 5 washes with cold IBS, the membranes were reacted with Lumiphos 53 (Boehringer Mannheim). The immunoreactive material was detected by fluorography and the typical results are shown in FIG. 9. Strong positive signals corresponding to single colonies were detected in the IPTG-induced samples. These colonies were picked from the master plate and found to carry the α-CKMB scFv-EE tag-traA vector. The colonies corresponding to negative signal on the film contained the control vector. The results indicate that the α-CKMB scFv-traA fusion protein is displayed of the bacterial surface and the single-chain antibody is folded into a biologically active conformation.

This method provides an easy rapid procedure for detecting recombinant single-chain antibody activity. It could be readily applied to screening libraries of recombinant antibody-traA fusion proteins. These libraries may include combinatorial single-chain gene banks of heavy and light variable region genes or mutational libraries of specific recombinant antibody genes. On the basis of the results indicating that the α-CKMB scFv-traA fusion protein is folded into a biologically active conformation, this method could have general application to detection of recombinant protein activities expressed on the surface of the bacterial cell colony. The activities to be detected could include binding activities, catalytic activities, inhibitory activities and altered structural conformations.

EXAMPLE 8

BACTERIOPHAGE/PILIN INTERACTION SYSTEM

Figure 12:
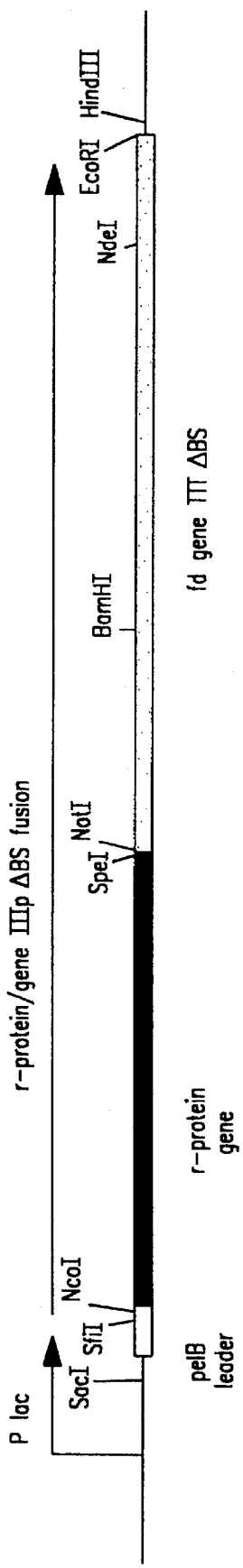
FIG. 12 shows the recombinant protein/gene III pΔBS fusion region.
Figure 13A:
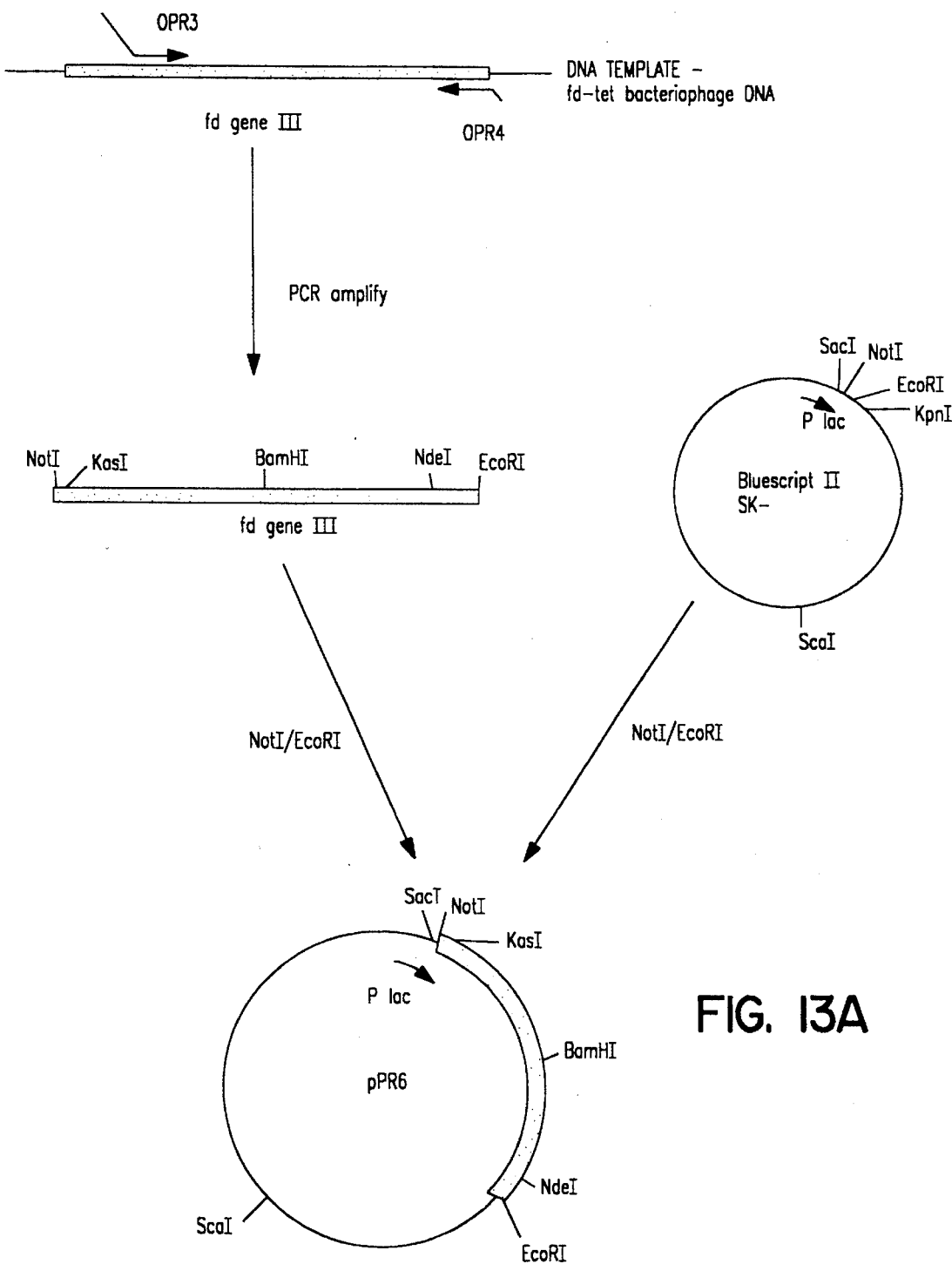
FIGS. 13A, 13B, 13C and 13D show the scheme for constructing the r-protein/gene III pΔBS display phagemid. SEQ10 NOS. 25 and 26 are set forth. The Oligonucleotides used in cloning are set forth below.
Figure 13B:
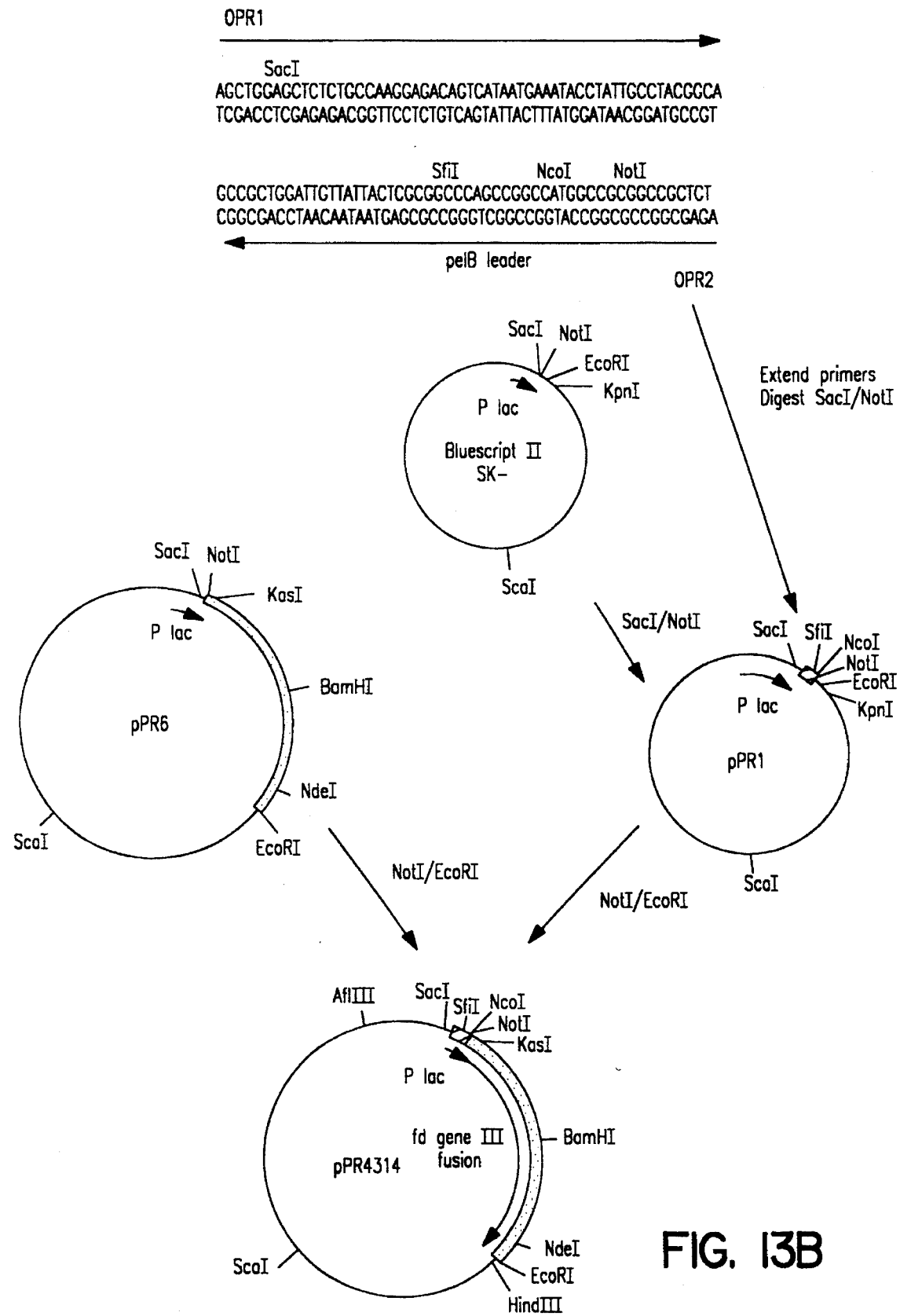
Figure 13C:
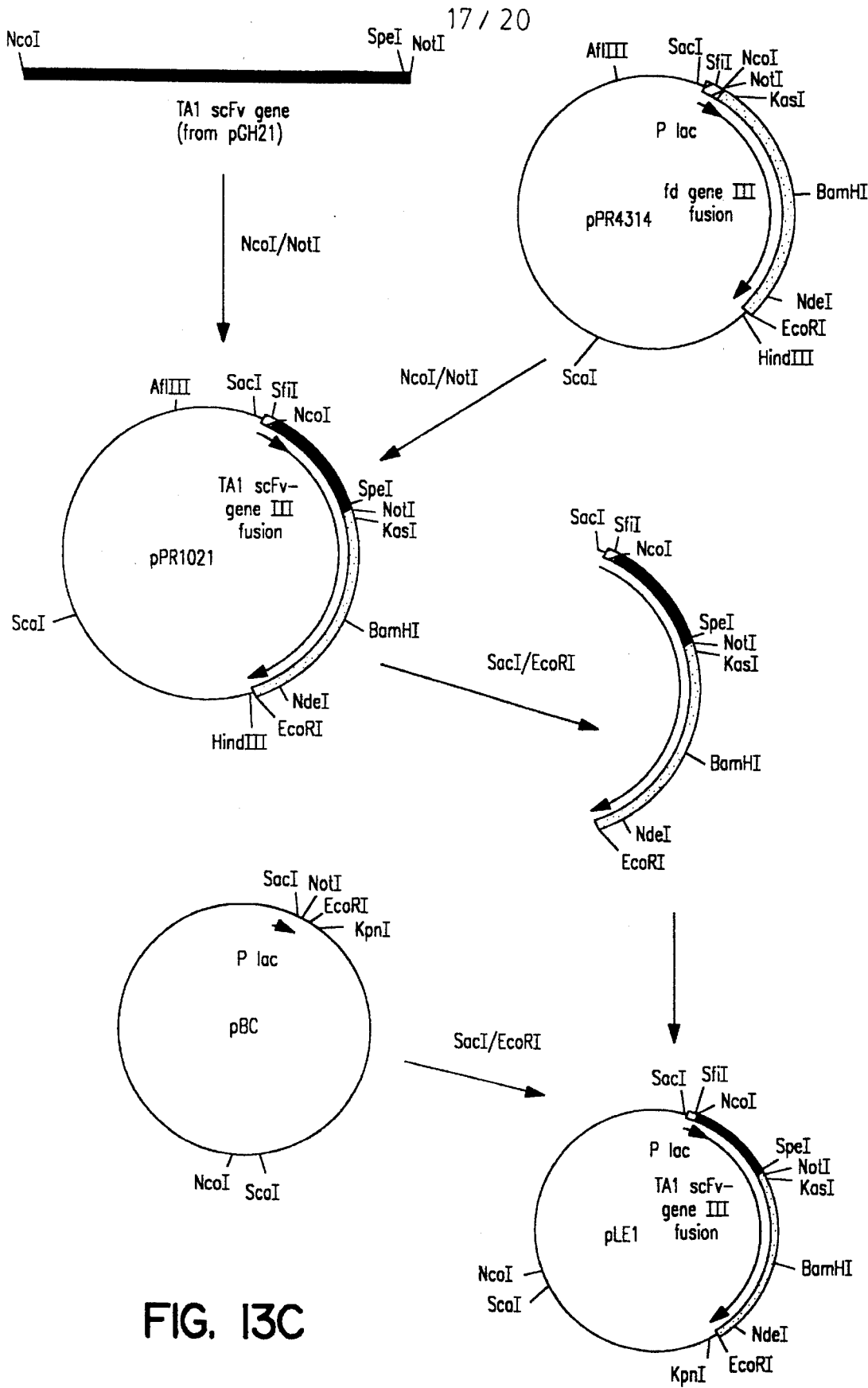
Figure 13D:
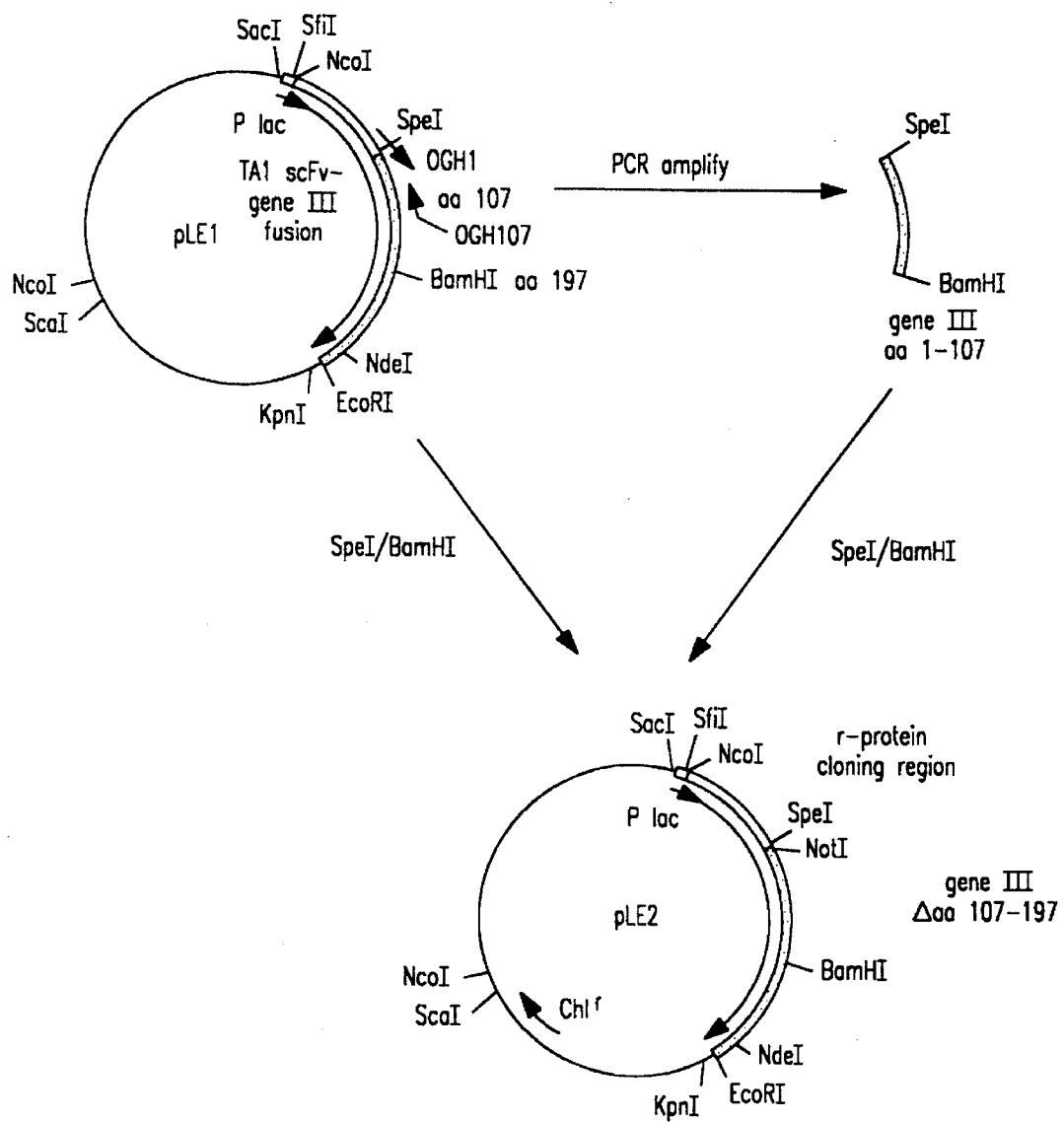

A phagemid vector was designed for the expression and display of geneIIIp ΔBS fusion proteins on the surface of the bacteriophage particle. The phagemid vector is based on the pBC phagemid vector (Stratagene) with features shown in FIG. 12. This vector carries the ColE1 replication origin for plasmid propagation, the f1 filamentous phage replication origin for recovery of phagemid DNA following co-infection with helper phage and the chloramphenicol resistance gene for antibiotic selection. The pelB leader and geneIIIp ΔBS DNA fragments were cloned downstream of the inducible lacZ promoter of pBC. The pelB leader was designed to allow for proper processing and display of the fusion protein on the bacteriophage particle. Cloning sites for NcoI, SfzI, SpeI, and NotI were incorporated between the pelB leader and geneIIIp ΔBS sequences to allow insertion of foreign DNA sequences. The steps involved in constructing this vector (referred to as LE2) are shown in FIG. 13.

The anti-EE tag scFv gene are isolated from monoclonal hybridoma mRNA as outlined in Example 2 and are inserted at the NotI and SpeI sites of LE2. An F' host strain, DH5-αF' [Woodcock, D: M. et al (1989) Nucl.Acids. Res. 17,3469–3478] is used to propagate these vectors by growth in media containing 30 μg/ml chloramphenicol.

In order to rescue phagemid particles, DH5-αF' cells carrying phagemid expression vector are transformed with the fKN16 phage DNA to tetracycline resistance. The fKN16 phage derivative was constructed from the tetracycline-resistance phage, fd-tet, by deleting a 507 bp segment of gene III (Nelson, et al., *Virology,* 108:338–350 (1981)). This phage is non-infective due to the gene III deletion but provides the helper phage proteins necessary for replication and packaging of the phagemid expression vector. DH5-αF' cells carrying both the phagemid expression vector and fKN16 are gown overnight in 100 ml of 2×YT media containing 30 μg/ml chloramphenicol and 15 μg/ml tetracycline. The cells are removed by centrifugation and the phage particles in the culture media are concentrated by precipitation with 5% PEG and 0.5M NaCl. The resulting phage particles carry either the fKN16 phage (tet$^r$) or the geneIIIp ΔBS phagemid vector (chl$^r$). Both the defective fKN16 gene protein and the anti-EE tag scFv-geneIIIp ΔBS fusion protein are displayed on the bacteriophage surface. The rescued phage are used to infect XL-1B cells carrying the EE tag-traA fusion vector. Since these cell express the EE tag antigen on their pili, the bacteriophage displaying the anti-EE tag scFv-geneIIIp ΔBS fusion protein bind the EE tag-traA fusion protein and infect these cells resulting in chloramphenicol resistant clones carrying the phagemid expression vector.

Figure 14:
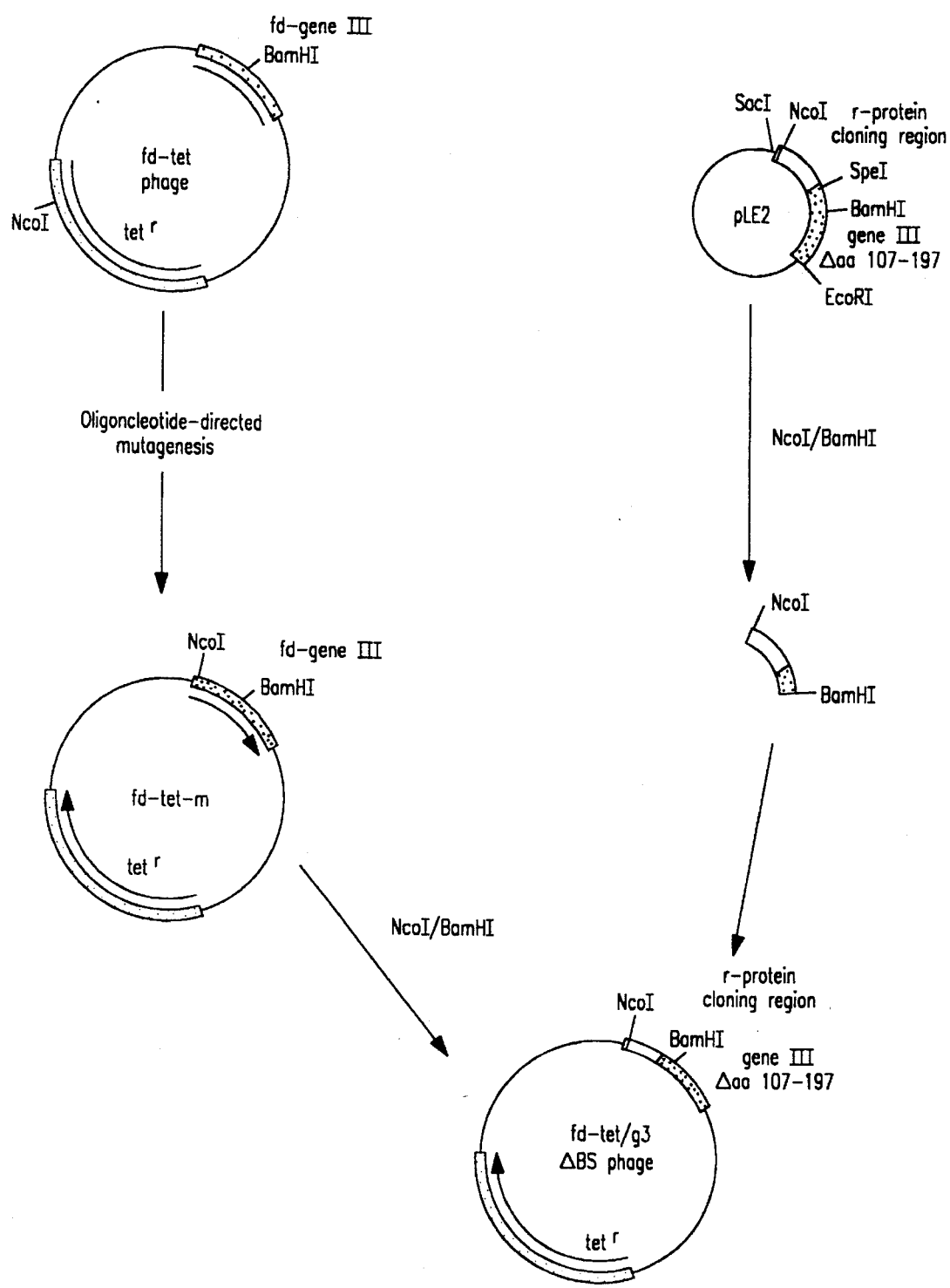
FIG. 14 shows the construction of the r-protein/gene III pΔBS display phage vector.

A bacteriophage vector based system can also be constructed for the display of recombinant proteins. The expression vector can be constructed from the fd-tet phage by replacing the normal geneIII with the anti-EE tag scFv-geneIIIp ΔBS fusion gene as outlined in FIG. 14. DH5-αF' cells are transformed to tetracycline resistance with the phage expression vector. The transformed cells are grown overnight in 100 ml of 2×YT media containing 15 μg/ml tetracycline. The cells will be removed by centrifugation and the phage particles in the culture media will be concentrated by precipitation with 5% PEG and 0.5M NaCl. The resulting phage particles will carry the geneIIIp ΔBS phage vector and display the anti-EE tag scFv-geneIIIp ΔBS fusion protein of the bacteriophage surface. These phage particles will be used to infect DH5-αF' cells carrying the EE tag-traA fusion vector.

Infectivity can then be tested by selection of tetracycline resistant colonies on agar plates as described for the phagemid system. Alternatively, since the expression phage is able to replicate and re-infect bacteria displaying the EE tag, infectivity can be characterized by the formation of plaques on a lawn of the display bacteria or the propagation of the phage in liquid cultures of the display bacteria. Plaque size or phage titer in the liquid media provide an indication of the strength of the recombinant protein-protein interactions responsible for the phage infectivity and propagation. In other words, the highest affinity recombinant protein-protein interactions between the display phage and the display bacteria provide the highest infectivity rates. The specificity of the infection can also be tested with cells that do not display the EE tag antigen.

This system is useful in screening libraries of recombinant protein such as scFvs. The phage displaying the high affinity scFv will infect and replicate in the antigen displaying bacteria at a higher rate that the phage displaying low affinity scFv. Thus, the phage displaying the high affinity scFv will be selectively enriched with continued growth of the culture. The resulting phage DNA can be isolated and the candidate scFv genes and proteins could be further characterized by sequence and affinity analyses.

It should be understood that the Examples and embodiments described herein are for illustrative purposes only and that various modifications or changes in light thereof will be suggested to persons skilled and purview of this Applications and the scope of the appended claims.

What is claimed is:

1. A method for isolating a member of a specific binding pair, comprising said member and an other member, said method comprising:

(a) expressing a fusion protein in a bacterial host which forms a pilus that is a receptor for bacteriophage attachment and infection, said fusion protein encoded by a chimeric DNA comprising a DNA segment encoding a leader amino acid sequence which mediates secretion of the fusion protein, a DNA segment encoding a pilin subunit which forms a pilus, and a DNA segment encoding said member;

(b) contacting the bacterial host of step (a) with a bacteriophage displaying an attachment protein wherein DNA encoding a pilin interaction domain has been substituted with DNA encoding the other member of the specific binding pair; and (c) selecting and then isolating bacterial host cells recognized by the bacteriophage, thereby isolating said member of the specific binding pair.

2. The method of claim 1, wherein said pilus is an F pilus.

3. The method of claim 2, wherein the bacteriophage is a filamentous bacteriophage or RNA bacteriophage.

4. The method of claim 3, wherein the bacteriophage is an fd bacteriophage.

5. The method of claim 1, wherein the DNA encoding the member is from a DNA library.

6. The method of claim 1, wherein the DNA encoding the other member is from a DNA library.

7. The method of claim 1, wherein the DNA encoding the member encodes an antigenic determinant and the DNA encoding the other member encodes an antibody.

8. The method of claim 1, wherein the DNA encoding the member encodes an antibody and the DNA encoding the other member encodes an antigenic determinant.

9. The method of claim 4, wherein the bacteriophage attachment protein is the gene III protein.

10. The method of claim 1, wherein the bacterial host recognized by the bacteriophage is selected by identification of a marker gene transferred from the bacteriophage to the host.

11. The method of claim 1, wherein the DNA encoding a member of the specific binding pair is mutagenized and specific binding pairs having an increased affinity are selected.

12. A method of screening for compounds affecting specific binding pair interaction comprising:

(a) contacting a bacterial cell having displayed on its surface a fusion protein comprised of pilin and a member of a specific binding pair, said specific binding pair comprised of the member and an other member, with a bacteriophage altered such that a pilin interaction domain is substituted by the other member of the specific binding pair;

(b) adding a test compound; and (c) measuring an effect of the test compound on the interaction between the bacteriophage and the bacterial cell, and thereby determining whether the test compound affects the specific binding pair interaction.

13. The method of claim 12, wherein the effect of the test compound on the interaction between the bacteriophage and the bacterial cell is measured by measuring the effect of the test compound on infectivity of the bacteriophage.

14. A method of screening for a member of a specific binding pair having increased binding affinity for an other member of the specific binding pair comprising:

(a) contacting a display bacterium displaying a fusion protein comprised of pilin and the other member of the specific binding pair with a bacteriophage altered such that a normal pilin binding domain is substituted with a protein from a library of proteins containing the member of the specific binding pair under conditions that allow bacteriophage infection; and (b) identifying specific binding pairs having increased binding affinity by identifying bacteriophage having an increased frequency of infectivity.

* * * * *

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
     ( A ) LENGTH: 35 base pairs
     ( B ) TYPE: nucleic acid
     ( C ) STRANDEDNESS: unknown
     ( D ) TOPOLOGY: unknown ( x i ) SEQUENCE DESCRIPTION: SEQ ID NO:1:

GGGGGGAATT CTATCCGAAA TTGAGGTAAC TTATG       3 5

( 2 ) INFORMATION FOR SEQ ID NO:2:

( i ) SEQUENCE CHARACTERISTICS:
     ( A ) LENGTH: 39 base pairs
     ( B ) TYPE: nucleic acid
     ( C ) STRANDEDNESS: unknown
     ( D ) TOPOLOGY: unknown ( x i ) SEQUENCE DESCRIPTION: SEQ ID NO:2:

GGGGGGTCTA GATTATCAGA GGCCAACGAC GGCCATAAC  39

( 2 ) INFORMATION FOR SEQ ID NO:3:

( i ) SEQUENCE CHARACTERISTICS:
        ( A ) LENGTH: 41 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:3:

GGGGGGATCC CCATGGCCAG CTGCGGGAAG AACATCATCA G  41

( 2 ) INFORMATION FOR SEQ ID NO:4:

( i ) SEQUENCE CHARACTERISTICS:
        ( A ) LENGTH: 40 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:4:

GGGGGGATCC GGCGCCGGCA GCAGTGGTCA GGACCTGATG  40

( 2 ) INFORMATION FOR SEQ ID NO:5:

( i ) SEQUENCE CHARACTERISTICS:
        ( A ) LENGTH: 33 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:5:

CACTTGGCCA TGGCCGAGGT TCAGCTGCAG CAG  33

( 2 ) INFORMATION FOR SEQ ID NO:6:

( i ) SEQUENCE CHARACTERISTICS:
        ( A ) LENGTH: 34 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:6:

GCTGCCACCG CCACCTGAGG AGACGGTGAC TGAG  34

( 2 ) INFORMATION FOR SEQ ID NO:7:

( i ) SEQUENCE CHARACTERISTICS:
        ( A ) LENGTH: 35 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:7:

GGAGGCGGCG GTTCTGATAT TGTGATGACT CAGGC  35

( 2 ) INFORMATION FOR SEQ ID NO:8:

( i ) SEQUENCE CHARACTERISTICS:
        ( A ) LENGTH: 40 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:8:

TTCATAGGCG GCCGCACTAG TAGCMCGTTT CAGYTCCARC    40

( 2 ) INFORMATION FOR SEQ ID NO:9:

( i ) SEQUENCE CHARACTERISTICS:
        ( A ) LENGTH: 33 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:9:

GCCGGCCATG GCCCAGGTBC ARCTKMARSA RTC    33

( 2 ) INFORMATION FOR SEQ ID NO:10:

( i ) SEQUENCE CHARACTERISTICS:
        ( A ) LENGTH: 35 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:10:

GCTGCCACCG CCACCTGMRG AGACDGTGAS TGARG    35

( 2 ) INFORMATION FOR SEQ ID NO:11:

( i ) SEQUENCE CHARACTERISTICS:
        ( A ) LENGTH: 35 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:11:

GGAGGCGGCG GTTCTGACAT TGTGMTGWCA CAGTC    35

( 2 ) INFORMATION FOR SEQ ID NO:12:

( i ) SEQUENCE CHARACTERISTICS:
        ( A ) LENGTH: 40 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:12:

TTCATAGGCG GCCGCACTAG TAGCMCGTTT KATYTCCARC    40

( 2 ) INFORMATION FOR SEQ ID NO:13:

( i ) SEQUENCE CHARACTERISTICS:
        ( A ) LENGTH: 45 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:13:

GGTGGCGGTG GCAGCGGCGG TGGTGGTTCC GGAGGCGGCG GTTCT    45

( 2 ) INFORMATION FOR SEQ ID NO:14:

( i ) SEQUENCE CHARACTERISTICS:
        ( A ) LENGTH: 45 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:14:

AGAACCGCCG CCTCCGGAAG GAGGACCGCC GCTGCCACCG CCACC    45

( 2 ) INFORMATION FOR SEQ ID NO:15:

( i ) SEQUENCE CHARACTERISTICS:
        ( A ) LENGTH: 53 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:15:

CATGGCGGCC GGCAGCGCGG CCGCTGAGGA AGAAGAGTAC ATGCCGATGG AAC     53

( 2 ) INFORMATION FOR SEQ ID NO:16:

( i ) SEQUENCE CHARACTERISTICS:
        ( A ) LENGTH: 53 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:16:

GCGCCTTCCA TCGGCATGTA CTCTTCTTCC TCAGCGGCCG CGCTGCCGGC CGC     53

( 2 ) INFORMATION FOR SEQ ID NO:17:

( i ) SEQUENCE CHARACTERISTICS:
        ( A ) LENGTH: 540 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:17:

GAAACAGCTA TGACCATGAT TACGAATTCT ATCCGAAATT GAGGTAACTT ATGAATGCTG     60

TTTTAAGTGT TCAGGGTGCT TCTGCGCCCG TCAAAAGAA GTCGTTTTTT TCCAAATTCA     120

CTCGTCTGAA TATGCTTCGC CTGGCTCGCG CAGTGATCCC GGCTGCTGTT CTGATGATGT     180

TCTTCCCGCA GCTGGCCATG GCGGCCGGCA GCGCGGCCGC TGAGGAAGAA GAGTACATGC     240

CGATGGAAGG CGCCGGCAGC AGTGGTCAGG ACCTGATGGC AAGCGGTAAC ACCACGGTTA     300

AGGCGACCTT CGGTAAGGAC TCCAGTGTTG TTAAATGGGT TGTTCTGGCT GAAGTTCTGG     360

TCGGTGCTGT CATGTACATG ATGACCAAAA ACGTCAAGTT CCTGGCCGGT TTTGCCATCA     420

TCTCTGTATT TATTGCTGTG GTTATGGCCG TCGTTGGCCT CTGATAATCT AGAGTCGACC     480

TGCAGGCATG CAAGCTTGGC ACTGGCCGTC GTTTTACAAC GTCGTGACTG GGAAAACCCT     540

( 2 ) INFORMATION FOR SEQ ID NO:18:

( i ) SEQUENCE CHARACTERISTICS:
        ( A ) LENGTH: 137 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:18:

Met Asn Ala Val Leu Ser Val Gln Gly Ala Ser Ala Pro Val Lys Lys
1               5                   10                  15

Lys Ser Phe Phe Ser Lys Phe Thr Arg Leu Asn Met Leu Arg Leu Ala
            20                  25                  30

Arg Ala Val Ile Pro Ala Ala Val Leu Met Met Phe Phe Pro Gln Leu
        35                  40                  45

Ala Met Ala Ala Gly Ser Ala Ala Ala Glu Glu Glu Glu Tyr Met Pro
    50                  55                  60

Met Glu Gly Ala Gly Ser Ser Gly Gln Asp Leu Met Ala Ser Gly Asn

|  | 65 |  |  |  |  | 70 |  |  |  |  | 75 |  |  |  |  | 80 |
| --- | --- | --- | --- | --- | --- | --- | --- | --- | --- | --- | --- | --- | --- | --- | --- | --- |
|  | Thr | Thr | Val | Lys | Ala | Thr | Phe | Gly | Lys | Asp | Ser | Ser | Val | Val | Lys | Trp |
|  |  |  |  |  | 85 |  |  |  |  | 90 |  |  |  |  | 95 |  |
|  | Val | Val | Leu | Ala | Glu | Val | Leu | Val | Gly | Ala | Val | Met | Tyr | Met | Met | Thr |
|  |  |  |  | 100 |  |  |  |  | 105 |  |  |  |  | 110 |  |  |
|  | Lys | Asn | Val | Lys | Phe | Leu | Ala | Gly | Phe | Ala | Ile | Ile | Ser | Val | Phe | Ile |
|  |  |  | 115 |  |  |  |  | 120 |  |  |  |  | 125 |  |  |  |
|  | Ala | Val | Val | Met | Ala | Val | Val | Gly | Leu |  |  |  |  |  |  |  |
|  |  | 130 |  |  |  |  | 135 |  |  |  |  |  |  |  |  |  |

( 2 ) INFORMATION FOR SEQ ID NO:19:

( i ) SEQUENCE CHARACTERISTICS:
        ( A ) LENGTH: 67 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:19:

```
GGGGGGAGCT CTCTGCAAAG AGACAGTCAT AATGAAATAC CTATTGCCTA CGGCAGCCGC    60

TGGATTG                                                             67
```

( 2 ) INFORMATION FOR SEQ ID NO:20:

( i ) SEQUENCE CHARACTERISTICS:
        ( A ) LENGTH: 66 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:20:

```
GGGGGCCGC GGCCGCGGCC ATGGCCGGCT GGGCCGCGAG TAATAACAAT CCAGCGGCTG    60

CCGTAG                                                             66
```

( 2 ) INFORMATION FOR SEQ ID NO:21:

( i ) SEQUENCE CHARACTERISTICS:
        ( A ) LENGTH: 84 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:21:

```
GGGGGCCGC GGCCGCGGAG GAAGAAGAGT ACAACCCGAA CGAAGGCGCC GCCTAGACTG    60

TTGAAAGTTG TTTAGCAAAA CCTC                                         84
```

( 2 ) INFORMATION FOR SEQ ID NO:22:

( i ) SEQUENCE CHARACTERISTICS:
        ( A ) LENGTH: 44 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:22:

```
GGGCCGAATT CCTATTAAGA CTCCTTATTA CGCAGTATGT TAGC                    44
```

( 2 ) INFORMATION FOR SEQ ID NO:23:

( i ) SEQUENCE CHARACTERISTICS:
        ( A ) LENGTH: 53 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:23:

GGGGGGACTA GTGCGGCCGC GGGCGCCGCT GAAACTGTTG AAAGTTGTTT AGC    53

( 2 ) INFORMATION FOR SEQ ID NO:24:

( i ) SEQUENCE CHARACTERISTICS:
        ( A ) LENGTH: 35 base pairs
        ( B ) TYPE: nucleic acid
        ( C ) STRANDEDNESS: unknown
        ( D ) TOPOLOGY: unknown ( x i ) SEQUENCE DESCRIPTION: SEQ ID NO:24:

GGGGGGGGAT CCAGAGGGTT GATATAAGTA TAGCC    35

( 2 ) INFORMATION FOR SEQ ID NO:25:

( i ) SEQUENCE CHARACTERISTICS:
        ( A ) LENGTH: 110 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:25:

AGCTGGAGCT CTCTGCCAAG GAGACAGTCA TAATGAAATA CCTATTGCCT ACGGCAGCCC    60

CTGGATTGTT ATTACTCGCG GCCCAGCCCG GCCATGGCCG CGGCCGCTCT    110

( 2 ) INFORMATION FOR SEQ ID NO:26:

( i ) SEQUENCE CHARACTERISTICS:
        ( A ) LENGTH: 110 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:26:

AGAGCGGCCC CGGCCATGCC CGGCTGGGCC GCGAGTAATA ACAATCCAGC GGCTGCCGTA    60

GGCAATAGGT ATTTCATTAT GACTGTCTCC TTGGCAAGAG AGCTCCAGCT    110